United States Patent
Dahl et al.

(10) Patent No.: US 7,276,222 B2
(45) Date of Patent: *Oct. 2, 2007

(54) DIAMONDOID-CONTAINING THERMALLY CONDUCTIVE MATERIALS

(75) Inventors: Jeremy E. Dahl, Palo Alto, CA (US); Robert M. Carlson, Petaluma, CA (US); Shenggao Liu, Hercules, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 10/892,037

(22) Filed: Jul. 14, 2004

(65) Prior Publication Data

US 2004/0262744 A1 Dec. 30, 2004

Related U.S. Application Data

(62) Division of application No. 10/047,044, filed on Jan. 14, 2002, now Pat. No. 6,783,589.

(60) Provisional application No. 60/262,842, filed on Jan. 19, 2001, provisional application No. 60/248,032, filed on Oct. 26, 2001, provisional application No. 60/341,921, filed on Dec. 18, 2001.

(51) Int. Cl.
  *C30B 29/04* (2006.01)
(52) U.S. Cl. ............... 423/446; 117/3; 117/4; 117/929
(58) Field of Classification Search ............ 117/3, 117/4, 929; 423/446
  See application file for complete search history.

(56) References Cited

U.S. PATENT DOCUMENTS 3,457,318 A 7/1969 Capaldi et al.
3,832,332 A 8/1974 Thompson
4,142,036 A 2/1979 Feinstein et al.

(Continued)

FOREIGN PATENT DOCUMENTS

| EP | 0450315 A1 | 10/1991 |
|---|---|---|
| EP | 0399851 | 11/1996 |
| EP | 1052307 A2 | 11/2000 |
| WO | WO92/13909 | 8/1992 |
| WO | WO95/06019 | 3/1995 |
| WO | WO95/11472 | 4/1995 |

OTHER PUBLICATIONS

Aczel, et al., "Stability of Adamantane and its Derivatives to Coal-liquefaction Conditions, and its implications toward the organic structure of Coal," *Fuel*, vol. 58, pp. 228-230, (Mar. 1979).

(Continued)

*Primary Examiner*—Robert Kunemund
(74) *Attorney, Agent, or Firm*—E. Joseph Gess

(57) ABSTRACT

Novel uses of diamondoid-containing materials in the field of microelectronics are disclosed. Embodiments include, but are not limited to, thermally conductive films in integrated circuit packaging, thermally conductive adhesive films, and thermally conductive films in thermoelectric cooling devices. The diamondoids employed in the present invention may be selected from lower diamondoids, as well as the newly provided higher diamondoids, including substituted and unsubstituted diamondoids. The higher diamondoids include tetramantane, pentamantane, hexamantane, heptamantane, octamantane, nonamantane, decamantane, and undecamantane. The diamondoid-containing material may be fabricated as a diamondoid-containing polymer, a diamondoid-containing sintered ceramic, a diamondoid ceramic composite, a CVD diamondoid film, a self-assembled diamondoid film, and a diamondoid-fullerene composite.

12 Claims, 18 Drawing Sheets

U.S. PATENT DOCUMENTS

| | | | |
|---|---|---|---|
| 4,273,561 A | 6/1981 | Fernandez-Moran Villalobos | |
| 4,952,747 A | 8/1990 | Alexander et al. | |
| 4,952,748 A | 8/1990 | Alexander et al. | |
| 4,952,749 A | 8/1990 | Alexander et al. | |
| 4,982,049 A | 1/1991 | Alexander et al. | |
| 4,996,079 A | 2/1991 | Itoh | |
| 5,015,758 A | 5/1991 | Pilgrim et al. | |
| 5,017,734 A | 5/1991 | Baum et al. | |
| 5,019,660 A | 5/1991 | Chapman et al. | |
| 5,019,665 A | 5/1991 | Partridge et al. | |
| 5,053,434 A | 10/1991 | Chapman | |
| 5,146,314 A | 9/1992 | Pankove | |
| 5,238,705 A | 8/1993 | Hayashi et al. | |
| 5,245,104 A | 9/1993 | Cullick | |
| 5,246,198 A | 9/1993 | Kurihara | |
| 5,256,391 A | 10/1993 | Chen et al. | |
| 5,268,513 A | 12/1993 | Shen | |
| 5,298,666 A | 3/1994 | Shen | |
| 5,306,851 A | 4/1994 | Wu et al. | |
| 5,308,661 A | 5/1994 | Feng et al. | |
| 5,313,094 A | 5/1994 | Beyer et al. | |
| 5,319,518 A | 6/1994 | Blood | |
| 5,347,063 A | 9/1994 | Shen et al. | |
| 5,367,051 A | 11/1994 | Narang et al. | |
| 5,369,213 A | 11/1994 | Shen | |
| 5,380,947 A | 1/1995 | Chen et al. | |
| 5,382,684 A | 1/1995 | Moini et al. | |
| 5,394,733 A | 3/1995 | Acholla | |
| 5,397,488 A | 3/1995 | Chen et al. | |
| 5,397,558 A | 3/1995 | Miyanaga et al. | |
| 5,410,092 A | 4/1995 | Shen | |
| 5,414,189 A | 5/1995 | Chen et al. | |
| 5,416,188 A | 5/1995 | Chiang et al. | |
| 5,430,193 A | 7/1995 | Shen | |
| 5,449,531 A | 9/1995 | Zhu et al. | |
| 5,455,072 A | 10/1995 | Bension et al. | |
| 5,461,184 A | 10/1995 | Swanson | |
| 5,462,680 A | 10/1995 | Brois et al. | |
| 5,462,776 A | 10/1995 | Gruen | |
| 5,498,812 A | 3/1996 | Bradway et al. | |
| 5,540,977 A | 7/1996 | Vogelsang et al. | |
| 5,547,748 A | 8/1996 | Ruoff et al. | |
| 5,576,355 A | 11/1996 | Chen et al. | |
| 5,578,901 A | 11/1996 | Blanchet-Fincher et al. | |
| 5,628,920 A | 5/1997 | Fuesser et al. | |
| 5,635,581 A | 6/1997 | Chiang et al. | |
| 5,695,847 A | 12/1997 | Browne | |
| 5,739,376 A | 4/1998 | Bingel | |
| 5,767,578 A | 6/1998 | Chang et al. | |
| 5,773,921 A | 6/1998 | Keesmann et al. | |
| 5,780,101 A | 7/1998 | Nolan et al. | |
| 5,849,130 A | 12/1998 | Browne | |
| 5,861,135 A | 1/1999 | Tanabe et al. | |
| 5,874,175 A | 2/1999 | Li | |
| 5,874,775 A | 2/1999 | Shiomi et al. | |
| 5,880,154 A | 3/1999 | Boukrinskaia et al. | |
| 5,907,189 A | 5/1999 | Mertol | |
| 5,925,465 A | 7/1999 | Ebbesen et al. | |
| 5,958,523 A | 9/1999 | Bradic | |
| 5,965,202 A | 10/1999 | Taylor-Smith et al. | |
| 5,976,909 A | 11/1999 | Shiomi et al. | |
| 6,080,470 A | 6/2000 | Dorfman | |
| 6,162,412 A | 12/2000 | Fujimori et al. | |
| 6,174,780 B1 | 1/2001 | Robinson | |
| 6,187,427 B1 | 2/2001 | Taylor-Smith et al. | |
| 6,211,463 B1 | 4/2001 | Fabis | |
| 6,222,113 B1 | 4/2001 | Ghoshal | |
| 6,235,851 B1 | 5/2001 | Ishii et al. | |
| 6,250,984 B1 | 6/2001 | Jin et al. | |
| 6,256,996 B1 | 7/2001 | Ghoshal | |
| 6,261,942 B1 | 7/2001 | Zhou et al. | |
| 6,277,766 B1 | 8/2001 | Ayers | |
| 6,286,212 B1 | 9/2001 | Eaton | |
| 6,300,410 B1 | 10/2001 | Shachat et al. | |
| 6,312,768 B1 | 11/2001 | Rode et al. | |
| 6,316,084 B1 | 11/2001 | Claus et al. | |
| 6,316,826 B1 | 11/2001 | Yamamoto et al. | |

OTHER PUBLICATIONS

Ansell, M., "Diamond Cleavage," publication unknown (4 pages), no date.

Balaban, et al., Systemic Classification and Nomenclature of Diamond Hydrocarbons-I, *Tetrahedron*, 34, pp. 3599-3606, (1978).

Badziag, P., et al., "Nanometre-sized Diamonds are More Stable than Graphite," *Nature*, vol. 343, pp. 244-245, and 517, (Jan. 1990).

Bagrii, Ye, et al., "Catalytic Breakdown of Paraffinic Hydrocarbons in the Presence of Adamantanes," *Petrol. Chem USSR*, vol. 30, No. 2, pp. 131-134, (1990).

Baughman, GL, "Dibromination of Adamantane," Publication Unknown, vol. 29, pp. 238-240 (Jan. 1964).

Bhushan, B., (editor), "Influence of Film Structure and Composition on Some Typical Properties," Modern Tribology Handbook, vol. Two, p. 891, no date.

Bhushan, B., (editor), "Self-Assembled Monolayers for Controlling Hydrophobicity and/or Friction and Wear," in *Modern Tribology Handbook*, Ch. 25, pp. 909-929, no date.

Bobrov, K., et al., "Atomic-scale Imaging of Insulting Diamond through Resonant Electron Injection," *Nature*, vol. 413, pp. 616-619 (Oct. 11, 2001).

Bott, Von K., "Synthese von Adamantan-und Norbornan chloressigsauren mit Trichlorathylen," *Angew. Chem.*, vol. 79, pp. 943-945 (1967).

Broich, F., "Carbonsauresynthesen mit 1,1-Dichlorathylen," *Angew. Chem.*, vol. 78, pp. 932-936 (1966).

Cammas, S., et al., "Poly(β-malic acid): Obtaining High Molecular Weights by Improvement of the Synthesis Route," *Polymer*, vol. 37, No. 18, pp. 4215-4220 (1996).

Chung, et al., Recent Developments in High-Energy Density Liquid Fuels, *Energy Fuels*, 13, pp. 641-649, (1999).

Courtney, T., et al., "The Chemistry of Diamantane: Part 1—Synthesis and Some Functionalisation Reactions," J.C.S.Perkin I, pp. 2691-2696 (1972).

Dahl, J., et al., Diamondoid Hydrocarbons as Indicators of Natural Oil Cracking, *Nature*, 399, pp. 54-57, (1999).

Das, M., (editor), "Diamond-Like Amorphous Carbon Films" as presented at Physics of Novel Materials, Proceedings of the Tenth Physics Summer Schoo.k, Canberra, Australia, Jan. 13-31, 1997, p. 221.

Dresselhaus, MS, et al., "Nanotechnology in Carbon Materials," *Nanotechnology*, Ch. 7, pp. 285-329, AIP Press (1999).

Drexler, Eric K., *Nanosystems: Molecular Machinery Manufacturing and Computation*, John Wiley & Sons, pp. 238-249, (1992).

Erdemir, Ali, et al., "Tribology of Diamond, Diamond-Like Carbon and Related Films," *Modern Tribology Handbook*, vol. Two, Ch. 24, CRC Press LLC, pp. 871-908, (1999).

Fort, Jr., et al., Adamantane: Consequences of the Diamondoid Structure, *Chem. Rev.*, 64, pp. 277-300, (1964).

Gruen, D.M., "Applications of Ultrananocrystalline Diamond Films," publication unknown, pp. 313-317 (Jan. 2000).

Gruen, D.M., "Microstructure and Grain Boundaries of Ultrananocrystalline Diamond Films," publication unknown, pp. 307-312, (Jan. 2000).

Gruen, D.M., "Nucleation of Ultrananocrystalline Diamond Films," publication unknown, pp. 303-306 (Jan. 2000).

Haaf, W., "Untersuchungen uber die Ritter-Reacktion," *Jahrg-96*, pp. 3359-3369 (1963) (In German).

Hala, V.S., et al., "Analyse Und Verwendung von Pyrolyseol," *Jahrgang*, pp. 85-88, (Feb. 1971) In German- English Abstract on p. 85.

Koch, H. et al., "Direkte Syntese der Adamantan-carbonsaure-(1)," *Eingengangen Am.*, 29, p. Z 944 (1960).

Kopidakis, G., et al., "Discrete Breathers in Realistic Models: Hydrocarbon Structures," *Physica B*, vol. 296, pp. 237-250 (2001).

Kulisch, W., "Nucleation of Diamond," *Deposition of Diamond-Like Superhard Materials*, Ch. 4.2, pp. 134-141, Springer-Verlag, Berlin-Heidelberg, (1999).

Kulisch, W., "Table 1. Physical Constants for $C_{60}$ Molecules and for Crystalline $C_{60}$," *Deposition of Diamond-Like Superhard Materials*, p. 290, Springer-Verlag, Berlin-Heidelberg, (1999).

Liaw, Der-Jang, et al., "Synthesis and Characterization of new Polyamides and Polyimides Prepared from 2,2-bis[4-(4-aminophenoxy)phenyl]adamantane," *Macromol. Chem. Phys.*, 200, No. 6, pp. 1326-1332 (1999).

Lifshitz, et al., "The Mechanism of Diamound Nucleation from Energetic Species", *Science* 297:1531-1533 (2002).

Lin, et al., Natrual Occurrence of Tetramantane ($C_{22}H_{23}$), Pentamantane ($C_{26}H_{32}$) and Hexamantane ($C_{30}H_{36}$) in a Deep Petroleum Reservoir, *Fuel*, 74:10, pp. 1512-1521, (1995).

McKervey, Synthetic Approaches to Large Diamondoid Hydrocarbons, *Tetrahedron*, 36, pp. 971-992, (1980).

Machacek, V., et al., "Let Od Objeveni Adamantanu," *Chemicke Listy/svazek*, 76, pp. 753-761, (1982) (Russian—English Abstract on p. 761).

Moine, L., et al., "Polymers of Malic Acid Conjugated with the 1-adamantyl Moiety as Lipophilic Pendant Group," *Polymer*, vol. 38, No. 12, pp. 3121-3127 (1997).

Moiseev, IK, et al., "Reactions of Adamantanes in Electrophilic Media," *Russian Chem. Reviews*, vol. 68, No. 12, pp. 1001-1120 (1999).

Oya, A, et al., "Carbonization of Adamantanes to a Graphitizable Carbon," *Fuel*, vol. 60, pp. 667-669, (Aug. 1981).

Petrov, A., "Hydrocarbons of Adamantane Series as Indices of Petroleum Catagenesis Process," *Advances in Organic Geo Chemistry*, 6th International Meeting on Organic Geochemistry, pp. 517-522 (1973).

Prawer, S., "The Wonderful World of Carbon," appearing in *Physics of Novel Materials*, Proceedings fo the Tenth Physics Summer School, Canberra, Australia, pp. 205-234, Jan. 13-31, 1997.

Prusova, D., Liquid Chromatography of Adamantanes and Carbon Adsorbents, *J. Chrom*, 234, pp. 1-11, (1982).

Piekarczyk, "Crystal Growth of CVD Diamond and Some of Its Peculiarities", *Crystal Research and Technology* 34(5-6):553-563 abs only (1999).

Rollmann, L., et al., "Adamantanes from Petroleum with Zeolites," *Catalyst Today*, vol. 31, pp. 163-169 (1996).

Rouhi, A., et al., "Tinkertoy Dreams: Someday, Computers May be Run by Electronic Circuits Based on Single Giant Molecules," *Science and Technology*, pp. 46-49 (Jul. 30, 2001).

Sandia National Laboratories (2000), World's First Diamond Micromachines Created at Sandia, Press Release, (Feb. 22, 2000), www.Sandia.gov.

Schleyer, P., et al., "Nonacyclo[11.7.1.1$^{2,18}$.0$^{3,16}$.0$^{4,13}$.0$^{5,10}$.0$^{6,14}$.0$^{7,11}$.0$^{15,20}$]-Docosane[1], a Bastard[2] Tetramantane," *J. of the Am. Chem. Soc.*, 90:8, letter to the editor, (Aug. 28, 1968).

Shen, M., et al., Finite $T_d$ Symmetry Models for Diamond: From Adamantane to Superadamantane ($C_{35}H_{36}$), *J. Am., Chem. Soc.*, vol. 114, No. 2, pp. 497-505, (1992).

Smith, G., et al., "Some Reactions of Adamantane and Adamantane Derivatives," *publication unknown*, vol. 26, pp. 2207-2212 (1961).

Stetter, H., et al., "Monofunktionelle Adamantan-Derivate," *Angew. Chem.*, vol. 71, pp. 429-430 (1959).

Supryadkina, N.Y., et al., "Catalytic Dealkylation of Alkyladamantanes," *Petrol. Chem., USSR*, vol. 28, No. 2, pp. 103-110, (1988).

Tachikawa, T., "Assembly and Packaging," *ULSI Technology*, Ch. 10, pp. 530-586, McGraw-Hill, (1996).

Timp, Gregory (editor), "Table 2.1—Diamond Like Materials," *Nanotechnology*, Ch. 2, p. 28, AIP Press (1999).

Tominaga, K., et al., "Next-generation Fine Chemicals Raw Material-Adamantane," *Chem. Econ. & Eng. Review*, vol. 17, No. 10, pp. 23-36 (Oct. 1985).

Vodicka, L, et al., "High Performance Liquid Chromatography of Halogeno Derivatives of Adamantane and Diamantane," *J. Chrom*, 270, pp. 199-205, (1983).

von R. Schleyer, P., et al., "The Preparation and Reactivity of 2-Substituted Derivatives of Adamantane" *Frick Chemical Laboratory*, vol. 83, pp. 182-187 (1961).

Windischmann, H., "CVD Diamond for Thermal Management," publication unknown, Chapter C2.2, pp. 410-415 (Jan. 2002).

Wingert, W., "G.c.-m.s. Analysis of Diamondoid Hydrocarbons in Smackover Petroleums," *Fuel*, vol. 71, pp. 37-42, (Jan. 1992).

Wolf, S., (editor), "Dielectric materials for Multilevel Interconnects," *Silicon Processing for the VLSI Era*, Ch. 4.3.2, pp. 194-199, Lattice Press, (1990).

Yokoyama, T., et al., "Selective Assembly on a Surface of Supramolecular Aggregates with Controlled Size and Shape," *Letters to Nature*, vol. 413, pp. 619-621, (Oct. 11, 2001).

Zhu, W., et al., "Novel Cold Cathode Materials," *Vacuum Microelectronics*, Ch. 6, pp. 247-287, John Wiley & Sons, Inc., (2001).

DIAMONDOID-CONTAINING THERMALLY CONDUCTIVE MATERIALS

REFERENCE TO RELATED APPLICATIONS

The present application is a divisional of U.S. patent application Ser. No. 10/047,044, filed Jan. 14, 2002 now U.S. Pat. No. 6,783,598 which claims the benefit of U.S. Provisional Patent Application No. 60/262,842, filed Jan. 19, 2001, U.S. Provisional Patent Application No. 60/348,032, filed Oct. 26, 2001 and U.S. Provisional Patent Application No. 60/341,921, filed Dec. 18, 2001; all of which are hereby incorporated herein by reference in their entirety.

BACKGROUND OF THE INVENTION

1. Field of the Invention

Embodiments of the present invention are directed toward novel uses of both lower and higher diamondoid-containing materials in the field of microelectronics. These embodiments include, but are not limited to, the use of such materials as heat sinks in microelectronics packaging and thermally conductive films, including adhesive films, and thermoelectric cooling devices.

2. State of the Art

Carbon-containing materials offer a variety of potential uses in microelectronics. As an element, carbon displays a variety of different structures, some crystalline, some amorphous, and some having regions of both, but each form having a distinct and potentially useful set of properties.

A review of carbon's structure-property relationships has been presented by S. Prawer in a chapter titled "The Wonderful World of Carbon," in *Physics of Novel Materials* (World Scientific, Singapore, 1999), pp. 205-234. Prawer suggests the two most important parameters that may be used to predict the properties of a carbon-containing material are, first, the ratio of $sp^2$ to $sp^3$ bonding in a material, and second, microstructure, including the crystallite size of the material, i.e. the size of its individual grains.

Elemental carbon has the electronic structure $1s^2 2s^2 2p^2$, where the outer shell 2s and 2p electrons have the ability to hybridize according to two different schemes. The so-called $sp^3$ hybridization comprises four identical σ bonds arranged in a tetrahedral manner. The so-called $sp^2$-hybridization comprises three trigonal (as well as planar) σ bonds with an unhybridized p electron occupying a π orbital in a bond oriented perpendicular to the plane of the σ bonds. At the "extremes" of crystalline morphology are diamond and graphite. In diamond, the carbon atoms are tetrahedrally bonded with $sp^3$-hybridization. Graphite comprises planar "sheets" of $sp^2$-hybridized atoms, where the sheets interact weakly through perpendicularly oriented π bonds. Carbon exists in other morphologies as well, including amorphous forms called "diamond-like carbon," and the highly symmetrical spherical and rod-shaped structures called "fullerenes" and "nanotubes," respectively.

Diamond is an exceptional material because it scores highest (or lowest, depending on one's point of view) in a number of different categories of properties. Not only is it the hardest material known, but it has the highest thermal conductivity of any material at room temperature. It displays superb optical transparency from the infrared through the ultraviolet, has the highest refractive index of any clear material, and is an excellent electrical insulator because of its very wide bandgap. It also displays high electrical breakdown strength, and very high electron and hole mobilities. If diamond as a microelectronics material has a flaw, it would be that while diamond may be effectively doped with boron to make a p-type semiconductor, efforts to implant diamond with electron-donating elements such as phosphorus, to fabricate an n-type semiconductor, have thus far been unsuccessful.

Attempts to synthesize diamond films using chemical vapor deposition (CVD) techniques date back to about the early 1980's. An outcome of these efforts was the appearance of new forms of carbon largely amorphous in nature, yet containing a high degree of $sp^3$-hybridized bonds, and thus displaying many of the characteristics of diamond. To describe such films the term "diamond-like carbon" (DLC) was coined, although this term has no precise definition in the literature. In "The Wonderful World of Carbon," Prawer teaches that since most diamond-like materials display a mixture of bonding types, the proportion of carbon atoms which are four-fold coordinated (or $sp^3$-hybridized) is a measure of the "diamond-like" content of the material. Unhybridized p electrons associated with $sp^2$-hybridization form π bonds in these materials, where the π bonded electrons are predominantly delocalized. This gives rise to the enhanced electrical conductivity of materials with $sp^2$ bonding, such as graphite. In contrast, $sp^3$-hybridization results in the extremely hard, electrically insulating and transparent characteristics of diamond. The hydrogen content of a diamond-like material will be directly related to the type of bonding it has. In diamond-like materials the bandgap gets larger as the hydrogen content increases, and hardness often decreases. Not surprisingly, the loss of hydrogen from a diamond-like carbon film results in an increase in electrical activity and the loss of other diamond-like properties as well.

Nonetheless, it is generally accepted that the term "diamond-like carbon" may be used to describe two different classes of amorphous carbon films, one denoted as "a:C—H," because hydrogen acts to terminate dangling bonds on the surface of the film, and a second hydrogen-free version given the name "ta-C" because a majority of the carbon atoms are tetrahedrally coordinated with $sp^3$-hybridization. The remaining carbons of ta-C are surface atoms that are substantially $sp^2$-hybridized. In a:C—H, dangling bonds can relax to the $sp^2$ (graphitic) configuration. The role hydrogen plays in a:C—H is to prevent unterminated carbon atoms from relaxing to the graphite structure. The greater the $sp^3$ content the more "diamond-like" the material is in its properties such as thermal conductivity and electrical resistance.

In his review article, Prawer states that tetrahedral amorphous carbon (ta-C) is a random network showing short-range ordering that is limited to one or two nearest neighbors, and no long-range ordering. There may be present random carbon networks that may comprise 3, 4, 5, and 6-membered carbon rings. Typically, the maximum $sp^3$ content of a ta-C film is about 80 to 90 percent. Those carbon atoms that are $sp^2$ bonded tend to group into small clusters that prevent the formation of dangling bonds. The properties of ta-C depend primarily on the fraction of atoms having the $sp^3$, or diamond-like configuration. Unlike CVD diamond, there is no hydrogen in ta-C to passivate the surface and to prevent graphite-like structures from forming. The fact that graphite regions do not appear to form is attributed to the existence of isolated $sp^2$ bonding pairs and to compressive stresses that build up within the bulk of the material.

The microstructure of a diamond and/or diamond-like material further determines its properties, to some degree because the microstructure influences the type of bonding content. As discussed in "Microstructure and grain boundaries of ultrananocrystalline diamond films" by D. M. Gruen, in *Properties, Growth and Applications of Diamond*, edited by M. H. Nazaré and A. J. Neves (Inspec, London, 2001), pp. 307-312, recently efforts have been made to synthesize diamond having crystallite sizes in the "nano"

range rather than the "micro" range, with the result that grain boundary chemistries may differ dramatically from those observed in the bulk. Nanocrystalline diamond films have grain sizes in the three to five nanometer range, and it has been reported that nearly 10 percent of the carbon atoms in a nanocrystalline diamond film reside in grain boundaries.

In Gruen's chapter, the nanocrystalline diamond grain boundary is reported to be a high-energy, high angle twist grain boundary, where the carbon atoms are largely $\pi$-bonded. There may also be $sp^2$ bonded dimers, and chain segments with $sp^3$-hybridized dangling bonds. Nanocrystalline diamond is apparently electrically conductive, and it appears that the grain boundaries are responsible for the electrical conductivity. The author states that a nanocrystalline material is essentially a new type of diamond film whose properties are largely determined by the bonding of the carbons within grain boundaries.

Another allotrope of carbon known as the fullerenes (and their counterparts carbon nanotubes) has been discussed by M. S. Dresslehaus et al. in a chapter entitled "Nanotechnology and Carbon Materials," in *Nanotechnology* (Springer-Verlag, New York, 1999), pp. 285-329. Though discovered relatively recently, these materials already have a potential role in microelectronics applications. Fullerenes have an even number of carbon atoms arranged in the form of a closed hollow cage, wherein carbon-carbon bonds on the surface of the cage define a polyhedral structure. The fullerene in the greatest abundance is the $C_{60}$ molecule, although $C_{70}$ and $C_{80}$ fullerenes are also possible. Each carbon atom in the $C_{60}$ fullerene is trigonally bonded with $sp^2$-hybridization to three other carbon atoms.

$C_{60}$ fullerene is described by Dresslehaus as a "rolled up" graphine sheet forming a closed shell (where the term "graphine" means a single layer of crystalline graphite). Twenty of the 32 faces on the regular truncated icosahedron are hexagons, with the remaining 12 being pentagons. Every carbon atom in the $C_{60}$ fullerene sits on an equivalent lattice site, although the three bonds emanating from each atom are not equivalent. The four valence electrons of each carbon atom are involved in covalent bonding, so that two of the three bonds on the pentagon perimeter are electron-poor single bonds, and one bond between two hexagons is an electron-rich double bond. A fullerene such as $C_{60}$ is further stabilized by the Kekulé structure of alternating single and double bonds around the hexagonal face.

Dresslehaus et al. further teach that, electronically, the $C_{60}$ fullerene molecule has 60 $\pi$ electrons, one $\pi$ electronic state for each carbon atom. Since the highest occupied molecular orbital is fully occupied and the lowest un-occupied molecular orbital is completely empty, the $C_{60}$ fullerene is considered to be a semiconductor with very high resistivity. Fullerene molecules exhibit weak van der Waals cohesive interactive forces toward one another when aggregated as a solid.

The following table summarizes a few of the properties of diamond, DLC (both ta-C and a:C—H), graphite, and fullerenes:

| Property | Diamond | ta-C | a: C—H | Graphite | $C_{60}$ Fullerene |
|---|---|---|---|---|---|
| C—C bond length (nm) | 0.154 | ≈0.152 | | 0.141 | pentagon: 0.146 hexagon: 0.140 |
| Density (g/cm$^3$) | 3.51 | >3 | 0.9–2.2 | 2.27 | 1.72 |
| Hardness (Gpa) | 100 | >40 | <60 | soft | Ven der Waals |
| Thermal conductivity (W/mK) | 2000 | 100–700 | | 10 | 0.4 |
| Bandgap (eV) | 5.45 | ≈3 | 0.8–4.0 | metallic | 1.7 |
| Electrical resistivity ($\Omega$ cm) | >10$^{16}$ | 10$^{10}$ | 10$^2$–10$^{12}$ | 10$^{-3}$–1 | >10$^8$ |
| Refractive Index | 2.4 | 2–3 | 1.8–2.4 | — | — |

The data in the table is compiled from p. 290 of the Dresslehaus et al. reference cited above, p. 221 of the Prawer reference cited above, p. 891 a chapter by A. Erdemir et al. in "Tribology of Diamond, Diamond-Like Carbon, and Related Films," in *Modern Tribology Handbook*, Vol. Two, B. Bhushan, Ed. (CRC Press, Boca Raton, 2001), and p. 28 of "Deposition of Diamond-Like Superhard Materials," by W. Kulisch, (SpringerVerlag, New York, 1999).

A form of carbon not discussed extensively in the literature are "diamondoids." Diamondoids are bridged-ring cycloalkanes that comprise adamantane, diamantane, triamantane, and the tetramers, pentamers, hexamers, heptamers, octamers, nonamers, decamers, etc., of adamantane (tricyclo[3.3.1.1$^{3,7}$] decane), adamantane having the stoichiometric formula $C_{10}H_{16}$, in which various adamantane units are face-fused to form larger structures. These adamantane units are essentially subunits of diamondoids. The compounds have a "diamondoid" topology in that their carbon atom arrangements are superimposable on a fragment of an FCC (face centered cubic) diamond lattice.

Diamondoids are highly unusual forms of carbon because while they are hydrocarbons, with molecular sizes ranging in general from about 0.2 to 20 nm (averaged in various directions), they simultaneously display the electronic properties of an ultrananocrystalline diamond. As hydrocarbons they can self-assemble into a van der Waals solid, possibly in a repeating array with each diamondoid assembling in a specific orientation. The solid results from cohesive dispersive forces between adjacent C—H$_x$ groups, the forces more commonly seen in normal alkanes.

In diamond nanocrystallites the carbon atoms are entirely $sp^3$-hybridized, but because of the small size of the diamondoids, only a small fraction of the carbon atoms are bonded exclusively to other carbon atoms. The majority have at least one hydrogen nearest neighbor. Thus, the majority of the carbon atoms of a diamondoid occupy surface sites (or near surface sites), giving rise to electronic states that are significantly different energetically from bulk energy states. Accordingly, diamondoids are expected to have unusual electronic properties.

To the inventors' knowledge, adamantane and substituted adamantane are the only readily available diamondoids. Some diamantanes, substituted diamantanes, triamantanes, and substituted triamantanes have been studied, and only a single tetramantane has been synthesized. The remaining diamondoids are provided for the first time by the inventors, and are described in their co-pending U.S. Provisional Patent Applications Nos. 60/262,842, filed Jan. 19, 2001;

60/300,148, filed Jun. 21, 2001; 60/307,063, filed Jul. 20, 2001; 60/312,563, filed Aug. 15, 2001; 60/317,546, filed Sep. 5, 2001; 60/323,883, filed Sep. 20, 2001; 60/334,929, filed Dec. 4, 2001; and 60/334,938, filed Dec. 4, 2001, incorporated herein in their entirety by reference. Applicants further incorporate herein by reference, in their entirety, the non-provisional applications sharing these titles which were filed on Dec. 12, 2001. The diamondoids that are the subject of these co-pending applications have not been made available for study in the past, and to the inventors' knowledge they have never been used before in a microelectronics application.

SUMMARY OF THE INVENTION

Embodiments of the present invention are directed toward novel uses of diamondoid-containing materials in the field of microelectronics. Diamondoids are bridged-ring cycloalkanes. They comprise adamantane, diamantane, and triamantane, as well as the tetramers, pentamers, hexamers, heptamers, octamers, nonamers, decamers, etc., of adamantane (tricyclo[3.3.1.1$^{3,7}$] decane), in which various adamantane units are face-fused to form larger structures. The compounds have a "diamondoid" topology in that their carbon atom arrangements are superimposable on a fragment of an FCC diamond lattice. The present embodiments include, but are not limited to, thermally conductive films in integrated circuit (IC) packaging, low-k dielectric layers in integrated circuit multilevel interconnects, thermally conductive adhesive films, thermally conductive films in (Peltier-based) thermoelectric cooling devices, passivation films for integrated circuit devices, dielectric layers in SRAM and DRAM capacitors, and field emission cathodes, each application based upon incorporating one or more diamondoid-containing materials. The diamondoid-containing materials of the present invention may be fabricated as a diamondoid-containing polymer, a diamondoid-containing sintered ceramic, a diamondoid ceramic composite, a CVD diamondoid film, and a self-assembled diamondoid film. Diamondoid-containing materials further include diamondoid-fullerene composites.

DETAILED DESCRIPTION OF THE INVENTION

Figure 1:
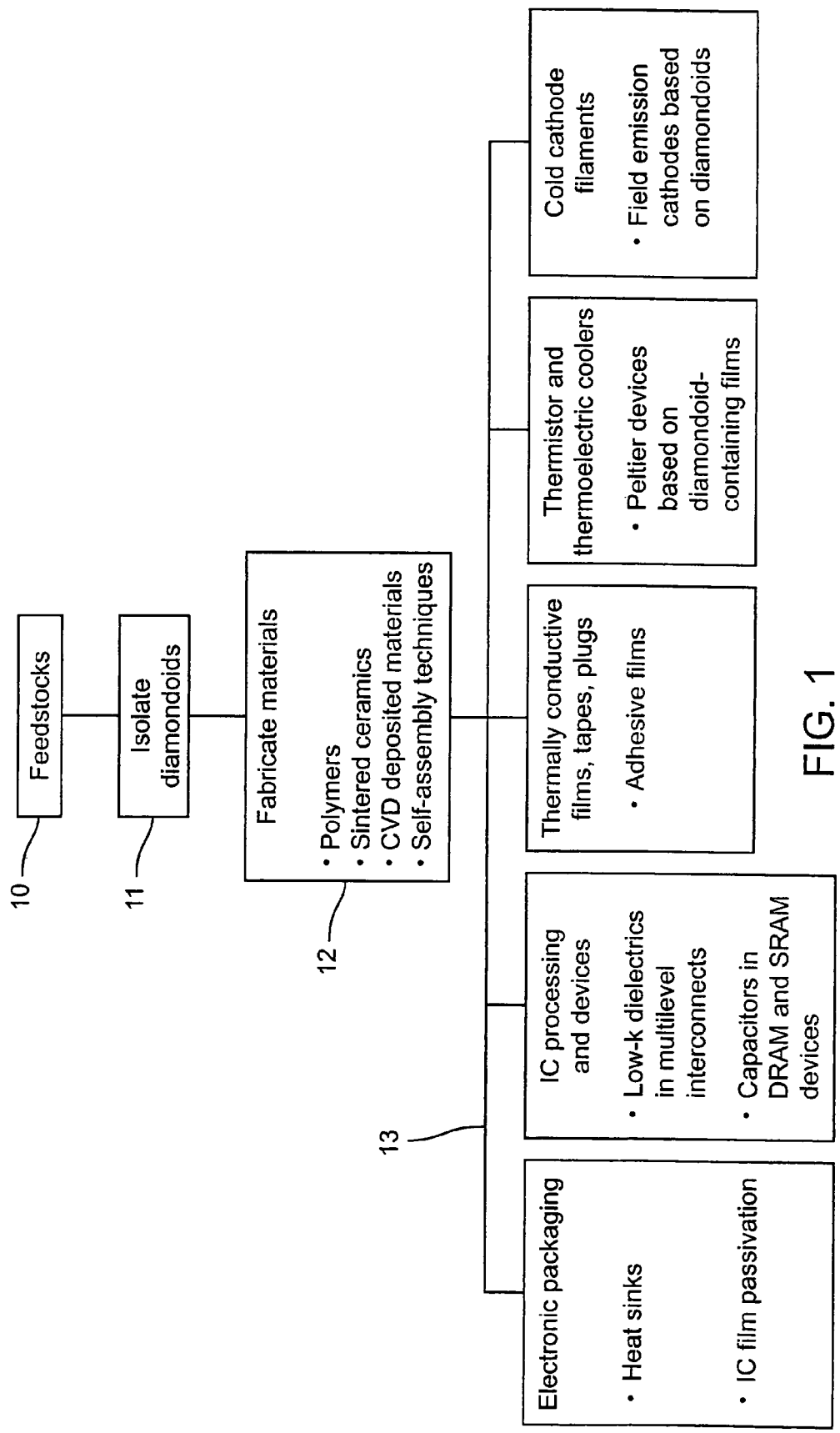
FIG. 1 schematically illustrates a process flow wherein diamondoids may be extracted from petroleum feedstocks, processed into a useful form, and then incorporated into a specific microelectronics application.

According to embodiments of the present invention, diamondoids are isolated from an appropriate feedstock, and then fabricated into a material that is specific for a particular microelectronics application. In the following discussion diamondoids will first be defined, followed by a description of how they may be recovered from petroleum feedstocks. After recovery diamondoids may be processed into polymers, sintered ceramics, and other forms of diamondoid-containing materials, depending on the application in which they are to be used.

Definition of Diamondoids

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like, including all isomers and stereoisomers thereof. The compounds have a "diamondoid" topology, which means their carbon atom arrangement is superimposable on a fragment of an FCC diamond lattice. Substituted diamondoids comprise from 1 to 10 and preferably 1 to 4 independently-selected alkyl substituents. Diamondoids include "lower diamondoids" and "higher diamondoids," as these terms are defined herein, as well as mixtures of any combination of lower and higher diamondoids.

The term "lower diamondoids refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids."

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above and isomers and stereoisomers of tetramantane, pentamantane, hexamantane, heptamantane, octamantane, nonamantane, decamantane, and undecamantane.

Adamantane chemistry has been reviewed by Fort, Jr. et al. in "Adamantane: Consequences of the Diamondoid Structure," *Chem. Rev.* vol. 64, pp. 277-300 (1964). Adamantane is the smallest member of the diamondoid series and may be thought of as a single cage crystalline subunit. Diamantane contains two subunits, triamantane three, tetramantane four, and so on. While there is only one isomeric form of adamantane, diamantane, and triamantane, there are four different isomers of tetramantane (two of which represent an enantiomeric pair), i.e., four different possible ways of arranging the four adamantane subunits. The number of possible isomers increases non-linearly with each higher member of the diamondoid series, pentamantane, hexamantane, heptamantane, octamantane, nonamantane, decamantane, etc.

Adamantane, which is commercially available, has been studied extensively. The studies have been directed toward a number of areas, such as thermodynamic stability, functionalization, and the properties of adamantane-containing materials. For instance, the following patents discuss materials comprising adamantane subunits: U.S. Pat. No. 3,457,318 teaches the preparation of polymers from alkenyl adamantanes; U.S. Pat. No. 3,832,332 teaches a polyamide polymer forms from alkyladamantane diamine; U.S. Pat. No. 5,017,734 discusses the formation of thermally stable resins from adamantane derivatives; and U.S. Pat. No. 6,235,851 reports the synthesis and polymerization of a variety of adamantane derivatives.

In contrast, the higher diamondoids, have received comparatively little attention in the scientific literature. McKervay et al. have reported the synthesis of anti-tetramantane in low yields using a laborious, multistep process in "Synthetic Approaches to Large Diamondoid Hydrocarbons," *Tetrahedron*, vol. 36, pp. 971-992 (1980). To the inventor's knowledge, this is the only higher diamondoid that has been synthesized to date. Lin et al. have suggested the existence of, but did not isolate, tetramantane, pentamantane, and hexamantane in deep petroleum reservoirs in light of mass spectroscopic studies, reported in "Natural Occurrence of Tetramantane ($C_{22}H_{28}$), Pentamantane ($C_{26}H_{32}$) and Hexamantane ($C_{30}H_{36}$) in a Deep Petroleum Reservoir," *Fuel*, vol. 74(10), pp. 1512-1521 (1995). The possible presence of tetramantane and pentamantane in pot material after a distillation of a diamondoid-containing feedstock has been discussed by Chen et al. in U.S. Pat. No. 5,414, 189.

The four tetramantane structures are iso-tetramantane [1(2)3], anti-tetramantane [121] and two enantiomers of skew-tetramantane [123], with the bracketed nomenclature for these diamondoids in accordance with a convention established by Balaban et al. in "Systematic Classification and Nomenclature of Diamond Hydrocarbons-I," *Tetrahedron* vol. 34, pp. 3599-3606 (1978). All four tetramantanes have the formula $C_{22}H_{28}$ (molecular weight 292). There are ten possible pentamantanes, nine having the molecular formula $C_{26}H_{32}$ (molecular weight 344) and among these nine, there are three pairs of enantiomers represented generally by [12(1)3], [1234], [1213] with the nine enantiomeric pentamantanes represented by [12(3)4], [1(2,3)4], [1212]. There also exists a pentamantane [1231] represented by the molecular formula $C_{25}H_{30}$ (molecular weight 330).

Hexamantanes exist in thirty-nine possible structures with twenty eight having the molecular formula $C_{30}H_{36}$ (molecular weight 396) and of these, six are symmetrical; ten hexamantanes have the molecular formula $C_{29}H_{34}$ (molecular weight 382) and the remaining hexamantane [12312] has the molecular formula $C_{26}H_{30}$ (molecular weight 342).

Heptamantanes are postulated to exist in 160 possible structures with 85 having the molecular formula $C_{34}H_{40}$ (molecular weight 448) and of these, seven are achiral, having no enantiomers. Of the remaining heptamantanes 67 have the molecular formula $C_{33}H_{38}$ (molecular weight 434), six have the molecular formula $C_{32}H_{36}$ (molecular weight 420) and the remaining two have the molecular formula $C_{30}H_{34}$ (molecular weight 394).

Octamantanes possess eight of the adamantane subunits and exist with five different molecular weights. Among the octamantanes, 18 have the molecular formula $C_{34}H_{38}$ (molecular weight 446). Octamantanes also have the molecular formula $C_{38}H_{44}$ (molecular weight 500); $C_{37}H_{42}$ (molecular weight 486); $C_{36}H_{40}$ (molecular weight 472), and $C_{33}H_{36}$ (molecular weight 432).

Nonamantanes exist within six families of different molecular weights having the following molecular formulas: $C_{42}H_{48}$ (molecular weight 552), $C_{41}H_{46}$ (molecular weight 538), $C_{40}H_{44}$ (molecular weight 524, $C_{38}H_{42}$ (molecular weight 498), $C_{37}H_{40}$ (molecular weight 484) and $C_{34}H_{36}$ (molecular weight 444).

Decamantane exists within families of seven different molecular weights. Among the decamantanes, there is a single decamantane having the molecular formula $C_{35}H_{36}$ (molecular weight 456) which is structurally compact in relation to the other decamantanes. The other decamantane families have the molecular formulas: $C_{46}H_{52}$ (molecular weight 604); $C_{45}H_{50}$ (molecular weight 590); $C_{44}H_{48}$ (molecular weight 576); $C_{42}H_{46}$ (molecular weight 550); $C_{41}H_{44}$ (molecular weight 536); and $C_{38}H_{40}$ (molecular weight 496).

Undecamantane exists within families of eight different molecular weights. Among the undecamantanes there are two undecamantanes having the molecular formula $C_{39}H_{40}$ (molecular weight 508) which are structurally compact in relation to the other undecamantanes. The other undecamantane families have the molecular formulas $C_{41}H_{42}$ (molecular weight 534); $C_{42}H_{44}$ (molecular weight 548); $C_{45}H_{48}$ (molecular weight 588); $C_{46}H_{50}$ (molecular weight 602);

$C_{48}H_{52}$ (molecular weight 628); $C_{49}H_{54}$ (molecular weight 642); and $C_{50}H_{56}$ (molecular weight 656).

FIG. 1 shows a process flow illustrated in schematic form, wherein diamondoids may be extracted from petroleum feedstocks 10 in a step 11, processed into a useful form in a step 12, and then incorporated into a specific microelectronics application shown generally at reference numeral 13.

Isolation of Diamondoids from Petroleum Feedstocks

Feedstocks that contain recoverable amounts of higher diamondoids include, for example, natural gas condensates and refinery streams resulting from cracking, distillation, coking processes, and the like. Particularly preferred feedstocks originate from the Norphlet Formation in the Gulf of Mexico and the LeDuc Formation in Canada.

These feedstocks contain large proportions of lower diamondoids (often as much as about two thirds) and lower but significant amounts of higher diamondoids (often as much as about 0.3 to 0.5 percent by weight). The processing of such feedstocks to remove non-diamondoids and to separate higher and lower diamondoids (if desired) can be carried out using, by way of example only, size separation techniques such as membranes, molecular sieves, etc., evaporation and thermal separators either under normal or reduced pressures, extractors, electrostatic separators, crystallization, chromatography, well head separators, and the like.

A preferred separation method typically includes distillation of the feedstock. This can remove low-boiling, non-diamondoid components. It can also remove or separate out lower and higher diamondoid components having a boiling point less than that of the higher diamondoid(s) selected for isolation. In either instance, the lower cuts will be enriched in lower diamondoids and low boiling point non-diamondoid materials. Distillation can be operated to provide several cuts in the temperature range of interest to provide the initial isolation of the identified higher diamondoid. The cuts, which are enriched in higher diamondoids or the diamondoid of interest, are retained and may require further purification. Other methods for the removal of contaminants and further purification of an enriched diamondoid fraction can additionally include the following nonlimiting examples: size separation techniques, evaporation either under normal or reduced pressure, sublimation, crystallization, chromatography, well head separators, flash distillation, fixed and fluid bed reactors, reduced pressure, and the like.

The removal of non-diamondoids may also include a pyrolysis step either prior or subsequent to distillation. Pyrolysis is an effective method to remove hydrocarbonaceous, non-diamondoid components from the feedstock. It is effected by heating the feedstock under vacuum conditions, or in an inert atmosphere, to a temperature of at least about 390° C., and most preferably to a temperature in the range of about 410 to 450° C. Pyrolysis is continued for a sufficient length of time, and at a sufficiently high temperature, to thermally degrade at least about 10 percent by weight of the non-diamondoid components that were in the feed material prior to pyrolysis. More preferably at least about 50 percent by weight, and even more preferably at least 90 percent by weight of the non-diamondoids are thermally degraded.

While pyrolysis is preferred in one embodiment, it is not always necessary to facilitate the recovery, isolation or purification of diamondoids. Other separation methods may allow for the concentration of diamondoids to be sufficiently high given certain feedstocks such that direct purification methods such as chromatography including preparative gas chromatography and high performance liquid chromatography, crystallization, fractional sublimation may be used to isolate diamondoids.

Even after distillation or pyrolysis/distillation, further purification of the material may be desired to provide selected diamondoids for use in the compositions employed in this invention. Such purification techniques include chromatography, crystallization, thermal diffusion techniques, zone refining, progressive recrystallization, size separation, and the like. For instance, in one process, the recovered feedstock is subjected to the following additional procedures: 1) gravity column chromatography using silver nitrate impregnated silica gel; 2) two-column preparative capillary gas chromatography to isolate diamondoids; 3) crystallization to provide crystals of the highly concentrated diamondoids.

An alternative process is to use single or multiple column liquid chromatography, including high performance liquid chromatography, to isolate the diamondoids of interest. As above, multiple columns with different selectivities may be used. Further processing using these methods allow for more refined separations which can lead to a substantially pure component.

Detailed methods for processing feedstocks to obtain higher diamondoid compositions are set forth in U.S. Provisional Patent Application No. 60/262,842 filed Jan. 19, 2001; U.S. Provisional Patent Application No. 60/300,148 filed Jun. 21, 2001; and U.S. Provisional Patent Application No. 60/307,063 filed Jul. 20, 2001. These applications are herein incorporated by reference in their entirety.

Materials Preparation

The term "materials preparation" as used herein refers to processes that take the diamondoids of interest as they are isolated from feedstocks, and fabricate them into diamondoid-containing materials for use in microelectronic applications. These processes may include the derivatization of diamondoids, the polymerization of derivatized and underivatized diamondoids, the sintering of diamondoid components into ceramics and ceramic composites, the use of diamondoids as a carbon precursor in conventional CVD techniques, including the use of the diamondoids triamantane and higher to nucleate a diamond film using conventional CVD techniques (such as thermal CVD, laser CVD, plasma-enhanced or plasma-assisted CVD, electron beam CVD, and the like), and self-assembly techniques involving diamondoids.

Methods of forming diamondoid derivatives, and techniques for polymerizing derivatized diamondoids, are discussed in U.S. patent application Ser. No. 60/334,939, entitled "Polymerizable Higher Diamondoid Derivatives," by Shenggao Liu, Jeremy E. Dahl, and Robert M. Carlson, filed Dec. 4, 2001, and incorporated herein by reference in its entirety.

To fabricate a polymeric film containing diamondoid constituents, either as part of the main polymeric chain, or as side groups or branches off of the main chain, one first synthesizes a derivatized diamondoid molecule, that is to say, a diamondoid having at least one functional group substituting one of the original hydrogens. As discussed in that application, there are two major reaction sequences that may be used to derivatize higher diamondoids: nucleophilic ($S_N1$-type) and electrophilic ($S_E2$-type) substitution reactions.

$S_N1$-type reactions involve the generation of higher diamondoid carbocations, which subsequently react with various nucleophiles. Since tertiary (bridgehead) carbons of higher diamondoids are considerably more reactive then secondary carbons under $S_N1$ reaction conditions, substitution at a tertiary carbon is favored.

$S_E2$-type reactions involve an electrophilic substitution of a C—H bond via a five-coordinate carbocation intermediate. Of the two major reaction pathways that may be used for the functionalization of higher diamondoids, the $S_N1$-type may be more widely utilized for generating a variety of higher diamondoid derivatives. Mono and multi-brominated higher diamondoids are some of the most versatile intermediates for functionalizing higher diamondoids. These intermediates are used in, for example, the Koch-Haaf, Ritter, and Friedel-Crafts alkylation and arylation reactions. Although direct bromination of higher diamondoids is favored at bridgehead (tertiary) carbons, brominated derivatives may be substituted at secondary carbons as well. For the latter case, when synthesis is generally desired at secondary carbons, a free radical scheme is often employed.

Although the reaction pathways described above may be preferred in some embodiments of the present invention, many other reaction pathways may certainly be used as well to functionalize a higher diamondoid. These reaction sequences may be used to produce derivatized diamondoids having a variety of functional groups, such that the derivatives may include diamondoids that are halogenated with elements other than bromine, such as fluorine, alkylated diamondoids, nitrated diamondoids, hydroxylated diamondoids, carboxylated diamondoids, ethenylated diamondoids, and aminated diamondoids. See Table 2 of the co-pending application "Polymerizable Higher Diamondoid Derivatives" for a listing of exemplary substituents that may be attached to higher diamondoids.

Diamondoids, as well as diamondoid derivatives having substituents capable of entering into polymerizable reactions, may be subjected to suitable reaction conditions such that polymers are produced. The polymers may be homopolymers or heteropolymers, and the polymerizable diamondoid derivatives may be co-polymerized with non-diamondoid-containing monomers. Polymerization is typically carried out using one of the following methods: free radical polymerization, cationic, or anionic polymerization, and polycondensation. Procedures for inducing free radical, cationic, anionic polymerizations, and polycondensation reactions are well known in the art.

Free radical polymerization may occur spontaneously upon the absorption of an adequate amount of heat, ultraviolet light, or high-energy radiation. Typically, however, this polymerization process is enhanced by small amounts of a free radical initiator, such as peroxides, azo compounds, Lewis acids, and organometallic reagents. Free radical polymerization may use either non-derivatized or derivatized higher diamondoid monomers. As a result of the polymerization reaction a covalent bond is formed between diamondoid monomers such that the diamondoid becomes part of the main chain of the polymer. In another embodiment, the functional groups comprising substituents on a diamondoid may polymerize such that the diamondoids end up being attached to the main chain as side groups. Diamondoid having more than one functional group are capable of cross-linking polymeric chains together.

For cationic polymerization, a cationic catalyst may be used to promote the reaction. Suitable catalysts are Lewis acid catalysts, such as boron trifluoride and aluminum trichloride. These polymerization reactions are usually conducted in solution at low-temperature.

In anionic polymerizations, the derivatized diamondoid monomers are typically subjected to a strong nucleophilic agent. Such nucleophiles include, but are not limited to, Grignard reagents and other organometallic compounds. Anionic polymerizations are often facilitated by the removal of water and oxygen from the reaction medium.

Polycondensation reactions occur when the functional group of one diamondoid couples with the functional group of another; for example, an amine group of one diamondoid reacting with a carboxylic acid group of another, forming an amide linkage. In other words, one diamondoid may condense with another when the functional group of the first is a suitable nucleophile such as an alcohol, amine, or thiol group, and the functional group of the second is a suitable electrophile such as a carboxylic acid or epoxide group. Examples of higher diamondoid-containing polymers that may be formed via polycondensation reactions include polyesters, polyamides, and polyethers.

Figure 2A:
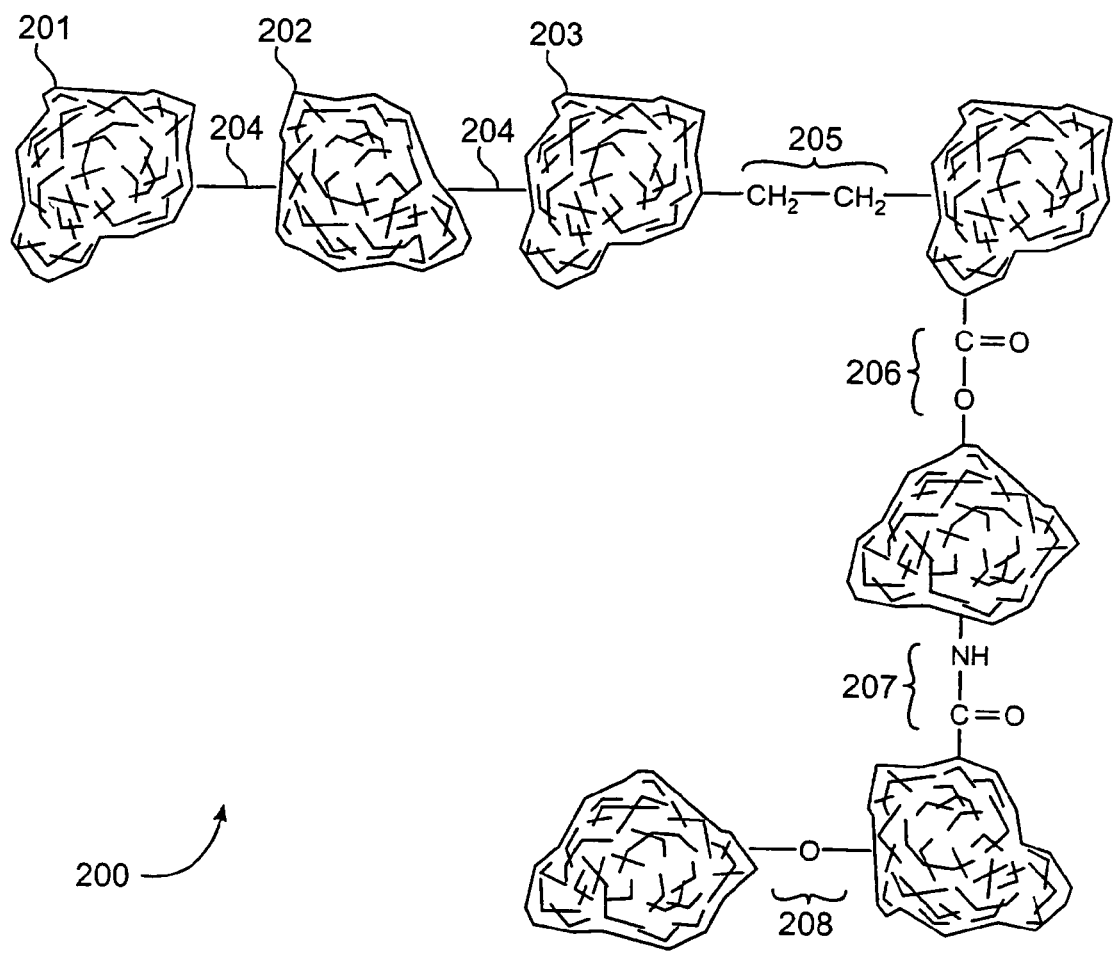
FIGS. 2A-C illustrate exemplary polymeric materials that may be fabricated from diamondoids.
Figure 2B:
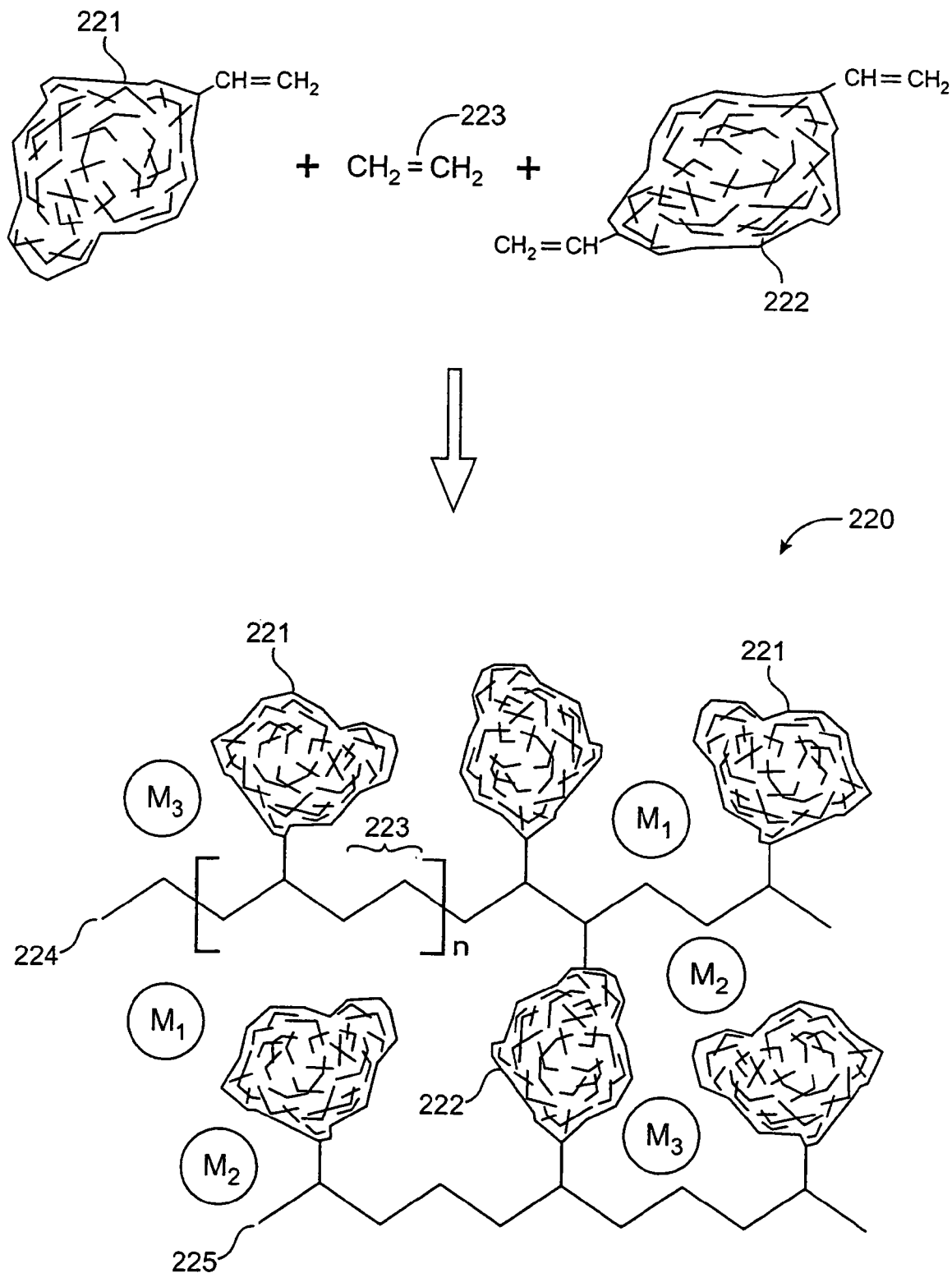
Figure 2C:
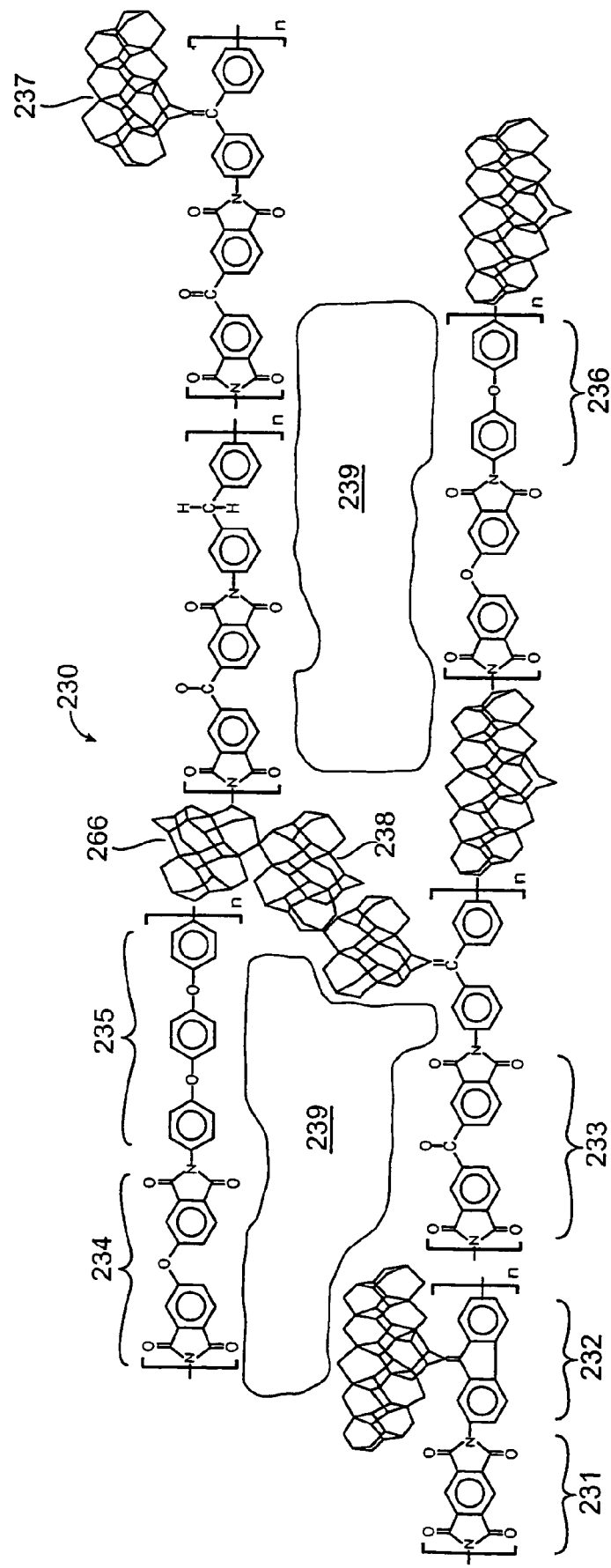

Exemplary diamondoid-containing polymeric films are illustrated schematically in FIGS. 2A-2C. Referring to FIG. 2A, a diamondoid-containing polymer is shown generally at 200, where the polymer comprises diamondoid monomers 201, 202, 203 linked through carbon-to-carbon covalent bonds 204. The diamondoid monomers 201, 202, 203 may comprise any member of the higher diamondoid series tetramantane through undecamantane. The covalent linkage 204 comprises a bond between two carbon atoms where each of carbon atoms of the bond are members of the two adjacent diamondoids. Stated another way, two diamondoids in the polymeric chain are directly linked such that there are no intervening carbon atoms that are not part of a diamondoid nucleus (or part of an adamantane subunit).

Alternatively, two adjacent diamondoids may be covalently linked through carbon atoms that are not members (part of the carbon nucleus) of either of the two diamondoids. Such a covalent linkage is shown schematically in FIG. 2A at reference numeral 205. As discussed above, adjacent diamondoids may be covalently connected through, for example, an ester linkages 206, an amide linkages 207, and an ether linkage is 208.

In an alternative embodiment, a diamondoid-containing polymer shown generally at 220 in FIG. 2B comprises a copolymer formed from the monomers ethylene and a higher diamondoid having at least one ethylene substituent. The diamondoid monomer shown at 221 contains one substituent ethylene group. The diamondoid monomer shown at 222 contains two ethylene substituents, and could have more than two substituents. Either or both of these diamondoids may be copolymerized with ethylene 223 itself, as a third monomer participating in the reaction, to form the co-polymer 220 or subunits thereof. Because the diamondoid monomer 222 has two substituent polymerizable moieties attached to it, this particular monomer is capable of cross-linking chains 224 and chain 225 together. Such a cross-linking reaction is capable of producing polymers having properties other than those of the polymer depicted in FIG. 2A, since for the FIG. 2A polymer the diamondoid nuclei are positioned within the main chain. A consequence of the structures formed in FIGS. 2A and 2B is that it is possible to incorporate metallic elements, particles, and inclusions (illustrated as M1 to M3) by inserting them into the interstices of folded and cross-linked polymeric chains. Diamondoid-containing materials may be doped in such a manner with alkali metals, alkali earth metals, halogens, rare earth elements, B, Al, Ga, In, Tl, V, Nb, and Ta to improve thermal conductivity if desired. The relative ratios of the monofunctional diamondoid monomer, the difunctional diamondoid monomer, and the ethylene monomer in the exemplary polymer of FIG. 2B may of course be adjusted to produce the desired properties with regard to stiffness, compactness, and ease of processing.

The exemplary polyimide-diamondoid polymer shown generally at 230 in FIG. 2C contains segments of polyimide chains derived from representative groups selected to illustrate certain relationships between structure and properties, in particular, how the properties of the exemplary polymer relate to the processing it has undergone. The dianhydride PMDA (pyromellitic dianhydride) shown at 231 and the diamine diaminofluorenone 232 are introduced into the chain for rigidity. The dianhydride BTDA (benzophenonetetracarboxylic dianhydride) shown at 233 provides the capability of further reaction at the carboxyl site, possibly for crosslinking purposes, and/or for the potential inclusion of metallic moieties into the material. The dianhydride oxydiphthalic dianhydride (ODPA) shown at 234, and the diamines oxydianiline (ODA) at 235 and bisaminophenoxybenzene at 236 may be introduced for chain flexibility and ease of processing of the material. Additionally, fluorinated dianhydrides such as 6FDA (not shown) may be introduced to lower the overall dielectric constant of the material.

The diamondoid components of the exemplary polymer illustrated schematically in FIG. 2C comprise a pentamantane diamondoid at 266, which is positioned in the main chain of the polymer, and an octamantane diamondoid at 237, which comprises a side group of the diamondoid-polyimide polymer at a position of a diamine (in this exemplary case, diaminobenzophenone) component. A diamondoid component 238 may be used as a cross-linking agent to connect two adjacent chains, through covalent linkages, or diamondoid component 238 may be passively present as an unfunctionalized "space filler" wherein it serves to separate main polymeric chains simply by steric hindrance. Folding of the main polymeric chains, particularly when diamondoid "fillers" 238 are present, may create voids 239, which may serve to reduce the overall dielectric constant of the material, since the dielectric constant of air (if it is the gas within the void), is one.

Figure 2D:
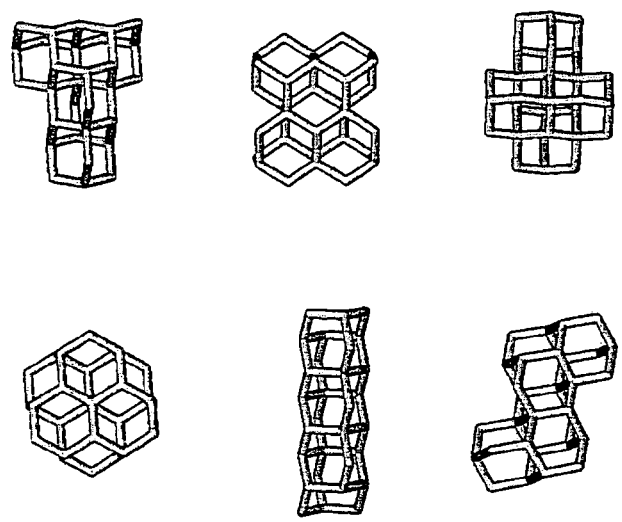
FIG. 2D illustrate the variety of three-dimensional shapes available among the highly symmetrical 396 molecular weight hexamantanes.
Figure 2E:
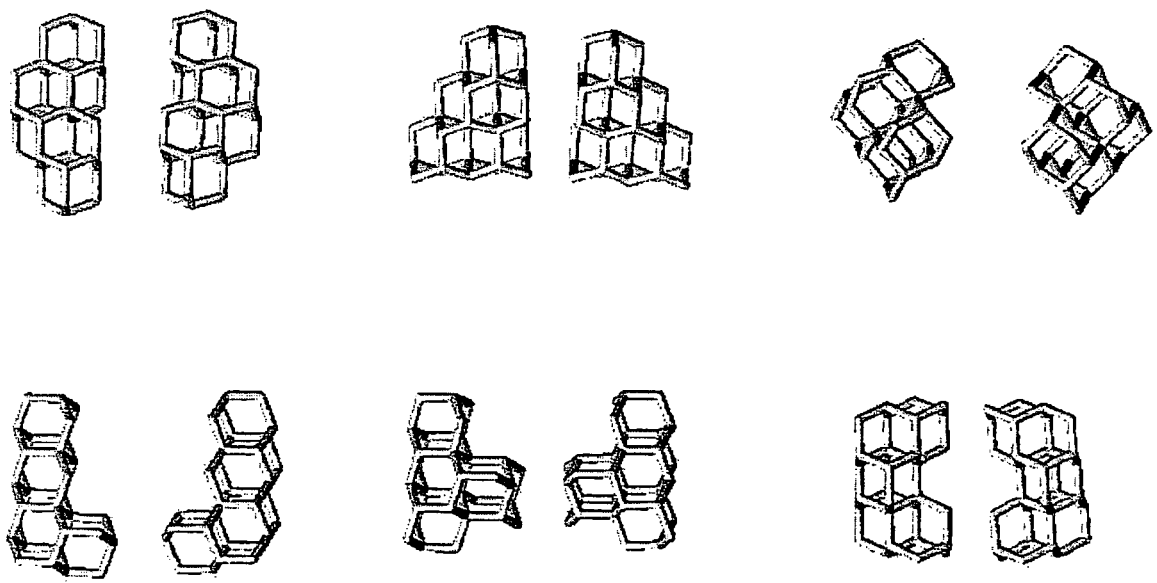
FIG. 2E illustrates the variety of three-dimensional shapes available among enantiomers of the chiral 396 molecular weight hexamantanes.

The diamond nanocrystallites (higher diamondoids) that may be incorporated into a diamondoid-containing material in general, and into polymeric materials in particular, have a variety of well-defined molecular structures, and thus they may be attached to each other, attached to a main polymer chain, used as cross-linking agents, etc., in a great variety of ways. The six hexamantanes illustrated in FIG. 2D are examples of a higher diamondoid having a highly symmetrical shape, and the 12 chiral hexamantanes illustrated in FIG. 2E are examples of enantiomeric pairs.

Figure 2H:
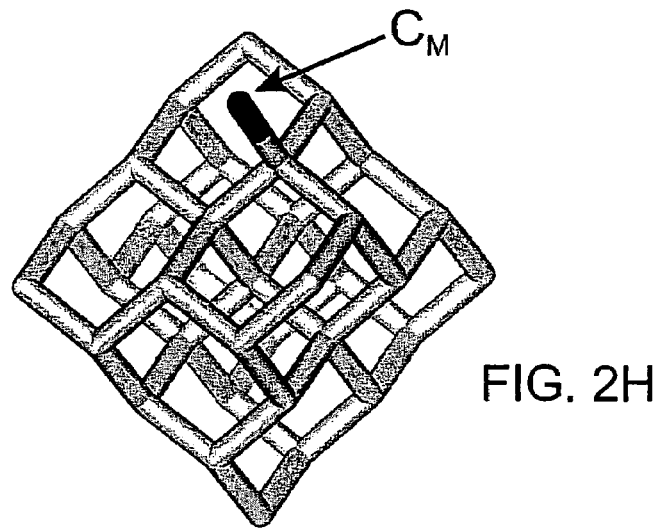
FIGS. 2F-H illustrates the variety of carbon attachment sites on a decamantane molecule, and how attachments to different sites in a polymer may result in cross-linked materials of variable rigidity.
Figure 2F:
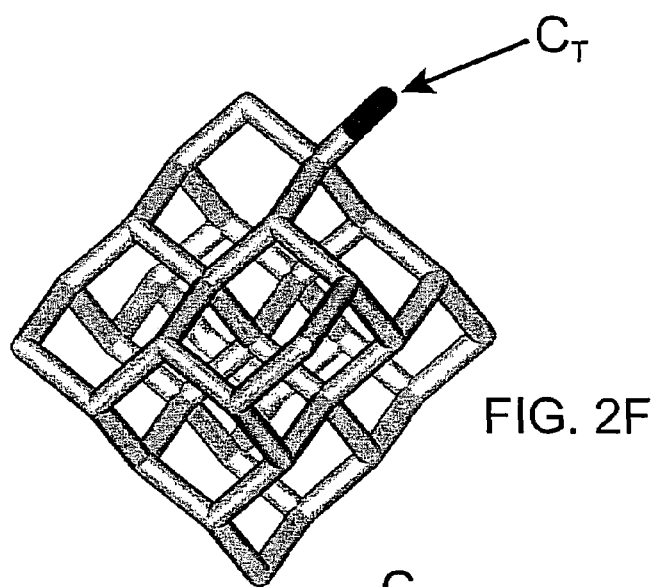
Figure 2G:
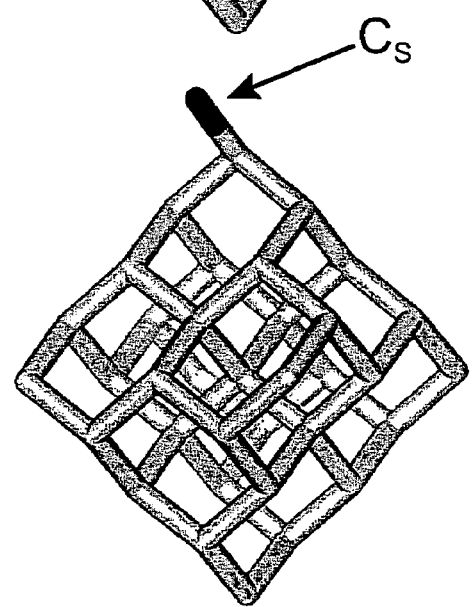

The molecular sites and the geometries of the attachments of a higher diamondoid to another diamondoid, and to a polymer chain, will also affect the properties of resulting materials. For example, the interconnection of higher diamondoid units through tertiary "bridge-head" carbons, as illustrated in FIG. 2F, will result in stronger, more rigid materials than those which result from interconnection through secondary carbons, as in FIG. 2G. Furthermore, attachment through tertiary carbons that are themselves bonded to the highest number of quaternary carbons in a higher diamondoid (nanocrystallite) will provide the strongest, most rigid materials, as in FIG. 2H.

Figure 2N:
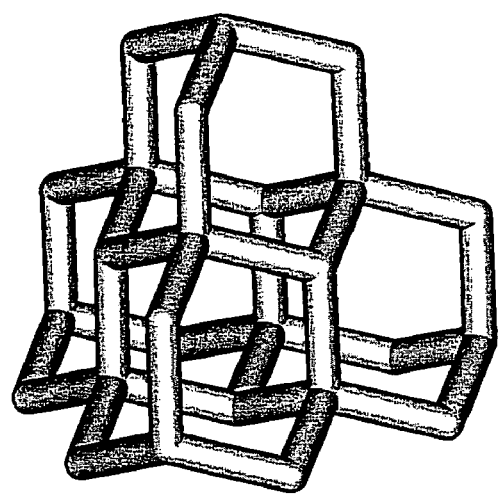
FIG. 2N illustrates [1(2,3)4] pentamantane.
Figure 2I:
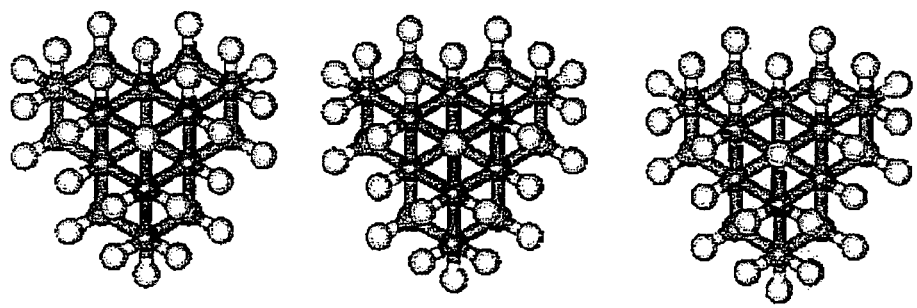
FIGS. 2I-K illustrate the manner in which a pentamantane may be oriented in a cross-linked polymer such that, in each case, the various diamond crystal lattice planes are substantially parallel.
Figure 2J:
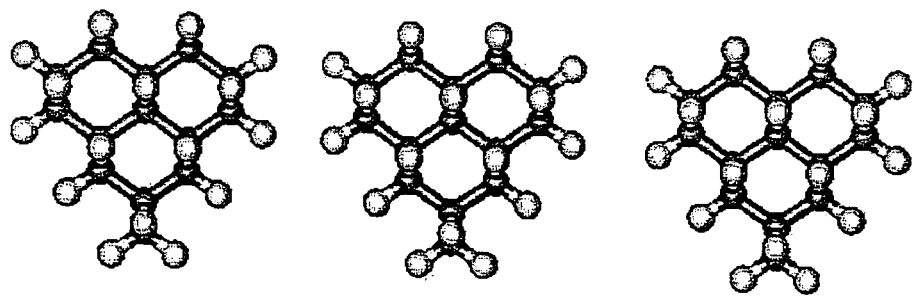
Figure 2K:
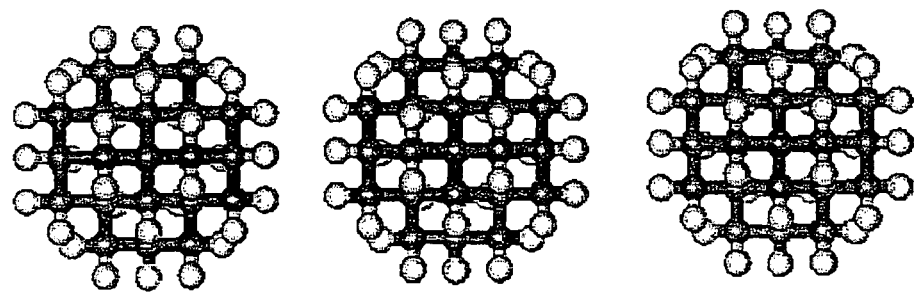
Figure 2L:
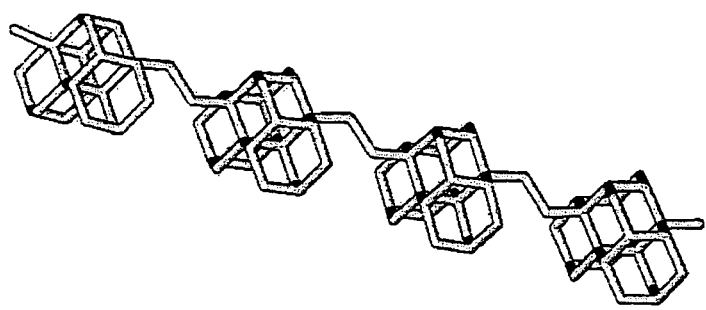
FIGS. 2L-M illustrate an exemplary chiral polymers prepared from enantiomers of [123] tetramantane.
Figure 2L:
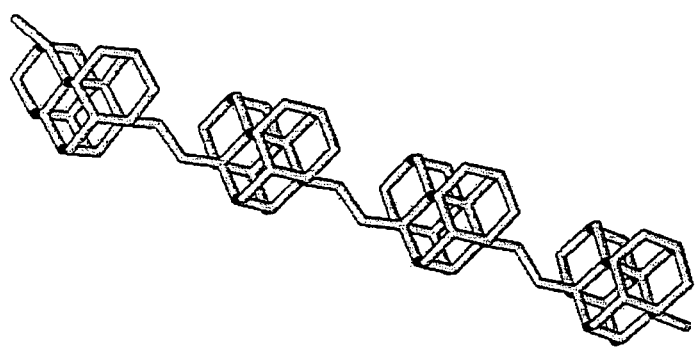
Figure 2M:
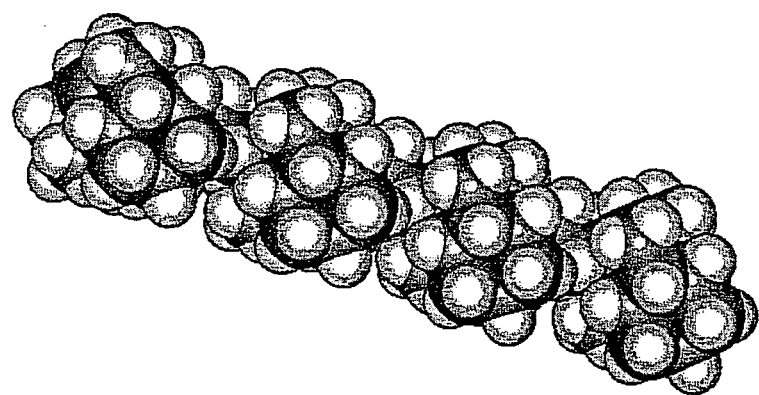
Figure 2M:
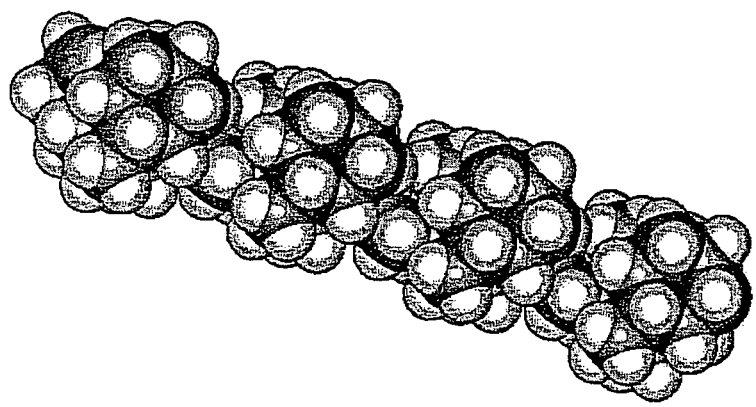

There are other properties of higher diamondoids that may be exploited to design new materials with desirable properties. Higher diamondoids display classical diamond crystal faces such as the (111), (110), and (100) planes, as shown in FIGS. 2I, 2J, and 2K for the diamondoid [1(2,3)4] pentamantane illustrated in FIG. 2N. These higher diamondoids may be oriented in materials such as polymers so that the resulting diamond nanocrystallites may have co-planer diamond faces. The diamondoids with chiral sturcture, may be used to fabricate the exemplary chiral polymers illustrated in FIGS. 2L, 2M. These kinds of chiral polymers have potential uses in photonics, and for the integration of photonic and electronic devices.

The diamondoid-containing polymers discussed above may be applied to a substrate undergoing microelectronic processing by any of methods known in the art, such as spin coating, molding, extrusion, and vapor phase deposition.

The weight of diamondoids and substituted diamondoids as a function of the total weight of the polymer (where the weight of the diamondoid functional groups are included in the diamondoid portion) may in one embodiment range from about 1 to 100 percent by weight. In another embodiment, the content of diamondoids and substituted diamondoids is about 10 to 100 percent by weight. In another embodiment, the proportion of diamondoids and substituted diamondoids in the polymer is about 25 to 100 percent by weight of the total weight of the polymer.

Another technique that may be used to form isolated diamondoids into useful and application-specific shapes is sintering, using processes that typically are used in the ceramics industry. Ceramics have been defined by M. Barsoum in *Fundamentals of Ceramics* (McGraw Hill, New York, 1997), pp. 2-3. In general, ceramics may be defined as solids formed by heating (often under pressure) mixtures of metals, nonmetallic elements such as nitrogen, oxygen, hydrogen, fluorine, and chlorine, and "nonmetallic elemental solids" including carbon, boron, phosphorus, and sulfur. Ceramics have varying degrees of ionic and covalent bonding. Many of the hardest, most refractory, and toughest ceramics are structures in which covalent bonding predominates. Examples of covalent ceramics are boron nitride (BN), silicon carbide (SiC), boron carbide ($B_4C$), silicon nitride ($Si_3N_4$). Although un-derivatized diamondoids will most likely form van der Waals solids with a certain cohesive energy exerted between adjacent surface carbons and their attached hydrogens, diamondoids may be derivatized as discussed above such that they possess functionality on their surfaces capable of interacting both ionically, and covalently, with other ceramic materials. Such solids may be thought of as behaving in general like a ceramic, but having small, diamond-like particulate inclusions.

Figure 3A:
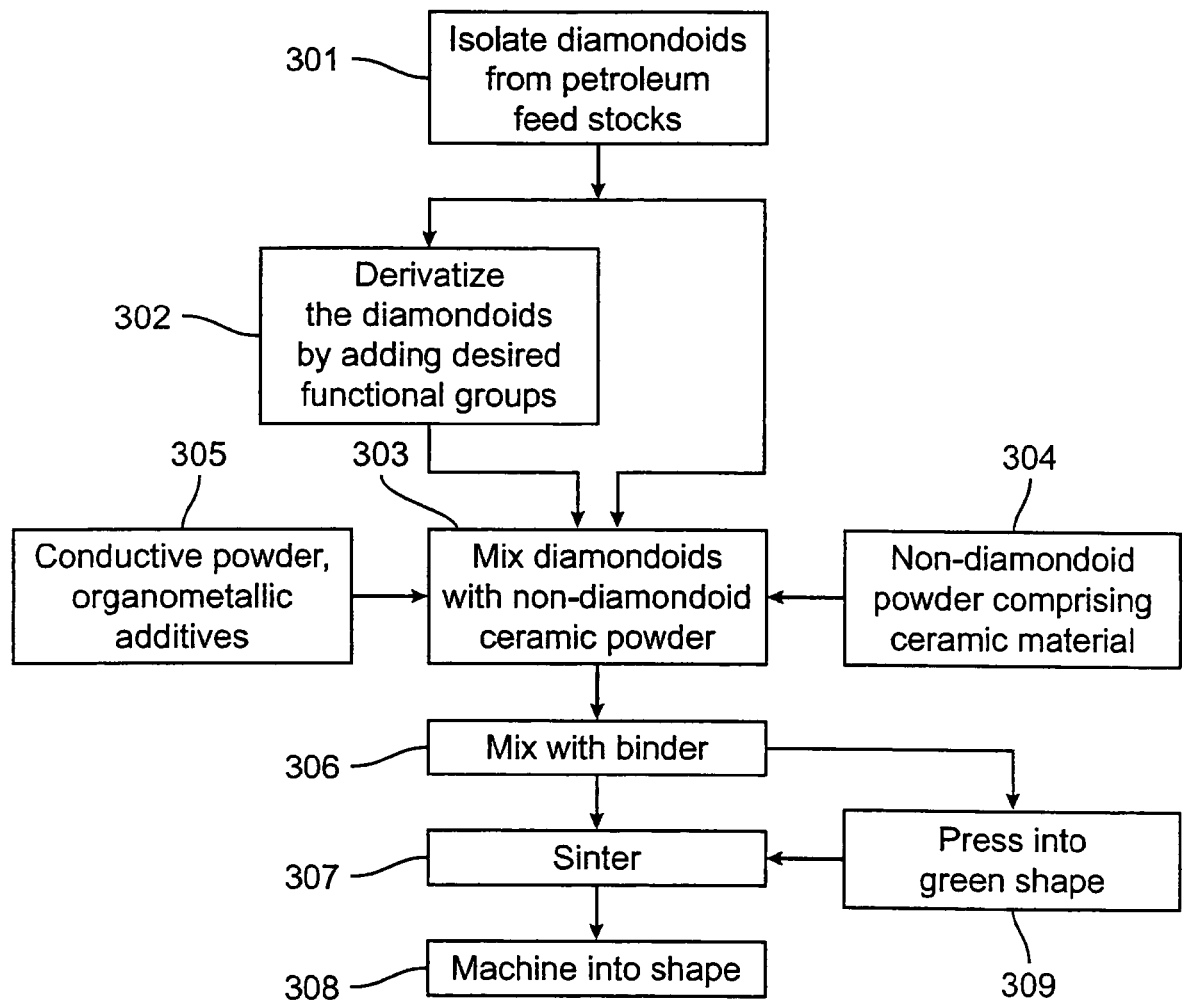
FIG. 3A illustrates in schematic form a process flow by which diamondoids may be sintered into ceramic-like materials and ceramic composites.

A process flow for generating the diamondoid-containing ceramic and/or ceramic composite is shown generally in FIG. 3A. Shown at reference numeral 301 is the isolation of diamondoids from feedstocks. The isolated diamondoids may then be derivatized with the desired functional groups as discussed above, as shown at 302. However, in some embodiments, it may not be necessary to derivatize the diamondoids. At 303, the diamondoids (which may or may not be derivatized) may be mixed with a nondiamondoid powder, the latter which may comprise any other ceramic materials known in the art. An exemplary list of such ceramics is given by Chiang et al. in "Physical Ceramics," Table 1.3 (Wiley, New York, 1997), incorporated herein in entirety by reference. It will be apparent to one skilled in the art that a substituent may be attached to the diamondoid, the substituent belonging to Group IA or Group IIA of the periodic table such that the the substituent will be an electron donor. Such elements are useful if a high degree of ionic character is desired. Examples of such elements include Li, Be, Na, Mg, K, Ca, and Sr. Alternatively, powders containing metal particles 305 from Groups IIIB to IIB may be mixed with the diamondoid materials including alloys of such metals. Noble metals such as Au, Ag, Pa, Pt and their alloys may be desirable since these materials are less susceptible to oxidation. Non-noble metals such as Cu, Ni, Fe, Co, Mo, W, V, Zn, and Ti, and their alloys, may also be used. Low melting point metals such as Sn, Al, Sb, In, Bi, Pb, and their alloys, or conventional low melting point solders may be mixed with the diamondoids, as well as semiconducting materials such as Si and Ge. The diamondoids may also be mixed with organometallic compounds to convey a desired degree of electrical conductivity to the resulting ceramic, and these organometallic compounds may react covalently with functional groups on the diamondoids.

The mixing of the functionalized and/or non-functionalized diamondoids with ceramic and/or metal powders is performed by way of example as a dry process, such as stirring or ball milling, or as a wet process forming a powder mixed slurry incorporating a liquid capable of being evaporated (such as alcohol, acetone, and water), optionally with the addition of a binder to improve the adhesion of the constituent particles to one another.

The mixture may then be sintered at elevated pressure and temperature, according to processes well known in the art, to yield a ceramic solid and/or ceramic composite. It may be preferable to machine the sintered product into a specific shape at 308, or the sintering product at 307 may be formed in a mold such that the sintered product has the desired shape. Prior to sintering, the mixture 306 may be pressed into a green shape 309 although this step is optional. The pressing step 309 is advantageous in some instances in that it may eliminate the trapping of gases, although it will be noted by one skilled in the art that in some applications a porosity is desired. The pressing step 309 may also allow soft metals, such as solders, if present, to flow within the system. In some embodiments, the pressing step 309 may be performed in conjunction with a vacuum applied to any or all of the mixture to facilitate shaping of the solid, or to remove undesired gaseous byproducts.

Figure 3B:
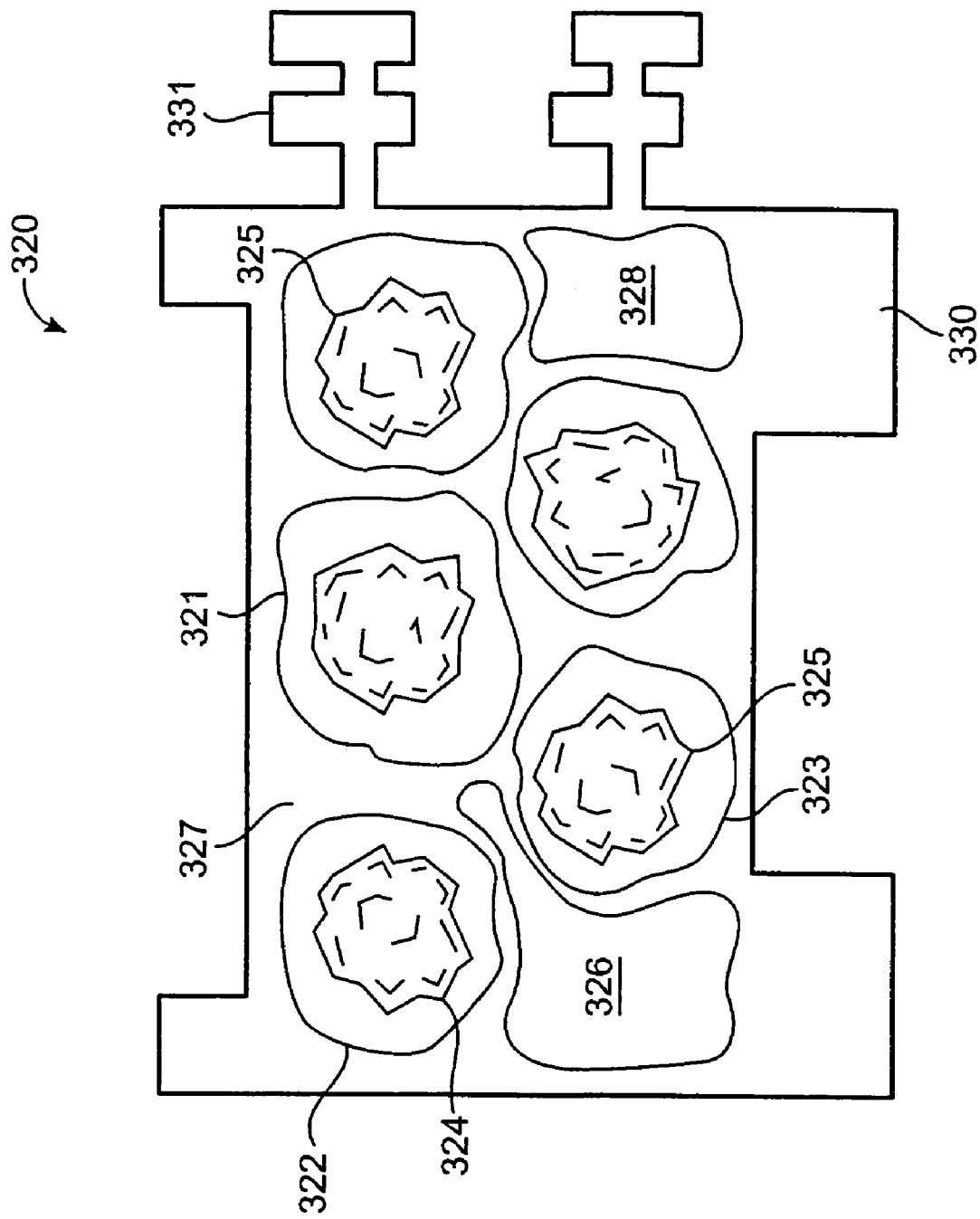
FIG. 3B illustrates in schematic form a diamondoid-containing ceramic part.

One such exemplary sintered diamondoid-containing ceramic and/or ceramic composite is illustrated schematically in FIG. 3B. The sintered diamondoid-containing ceramic is shown generally at 320, where diamondoid particles 321, 322, and 323 are shown. The diamondoid particle at 321 may be derivatized such that it is bound in the ceramic material by chemical bonds, or the diamondoids may be underivatized and bound in the material substantially by mechanical forces. In an alternative embodiment, the diamondoid particles and/or diamondoid aggregates at 322 and 323 may contain functional groups 324 and 325, respectively, to facilitate adhesion of the diamondoid particles to ceramic particles 326. Alternatively, a binder 327 may be present to facilitate adhesion of diamondoid particles 322 and 323 to ceramic particles 326, in some cases by forming covalent bonds through functional groups 324 and 325. Large metallic inclusions 328 may be present to facilitate electrical conduction.

The ceramic shown generally at 320 may be processed into specific shapes and forms, having for example protrusions 330 for nesting and positioning the ceramic in place, or regions 331 that may have specific active functions. The shaping step 308 (see again FIG. 3A) may be accomplished by any of the techniques known in the art, such as forging, machining, grinding, or stamping.

The weight of diamondoids and substituted diamondoids as a function of the total weight of the ceramic (where the weight of the diamondoid functional groups are included in the diamondoid portion) may in one embodiment range from about 1 to 99.9 percent by weight. In another embodiment, the content of diamondoids and substituted diamondoids is about 10 to 99 percent by weight. In another embodiment, the proportion of diamondoids and substituted diamondoids in the ceramic is about 25 to 95 percent by weight of the total weight of the ceramic.

Thus far, the present description has focused on polymerization and ceramic sintering as techniques for forming diamondoids into application specific forms. Two additional techniques, chemical vapor deposition (CVD) and self-assembly, will be discussed next. For instance, conventional methods of synthesizing diamond by plamsa enhanced chemical vapor deposition (PECVD) techniques are well known in the art, and date back to around the early 1980's. Although it is not necessary to discuss the specifics of these methods as they relate to the present invention, one point in particular that should be made since it is relevant to the role hydrogen plays in the synthesis of diamond by "conventional" plasma-CVD techniques.

In one method of synthesizing diamond films discussed by A. Erdemir et al. in "Tribology of Diamond, Diamond-Like Carbon, and Related Films," in *Modern Tribology Handbook*, Vol. Two, B. Bhushan, Ed. (CRC Press, Boca Raton, 2001) pp. 871-908, a modified microwave CVD reactor is used to deposit a nanocrystalline diamond film using a $C_{60}$ fullerene, or methane, gas carbon precursor. This method differs from conventional CVD techniques in that the deposition was conducted in the absence of hydrogen, with argon used instead. Methane/argon gas mixtures are being increasingly used when nanocrystalline diamond films are desired, as discussed above. To introduce the $C_{60}$ fullerene precursor into the reactor, a device called a "quartz transpirator" is attached to the reactor, wherein this device essentially heats a fullerene-rich soot to temperatures between about 550 and 600° C. to sublime the $C_{60}$ fullerene into the gas phase.

Figure 4:
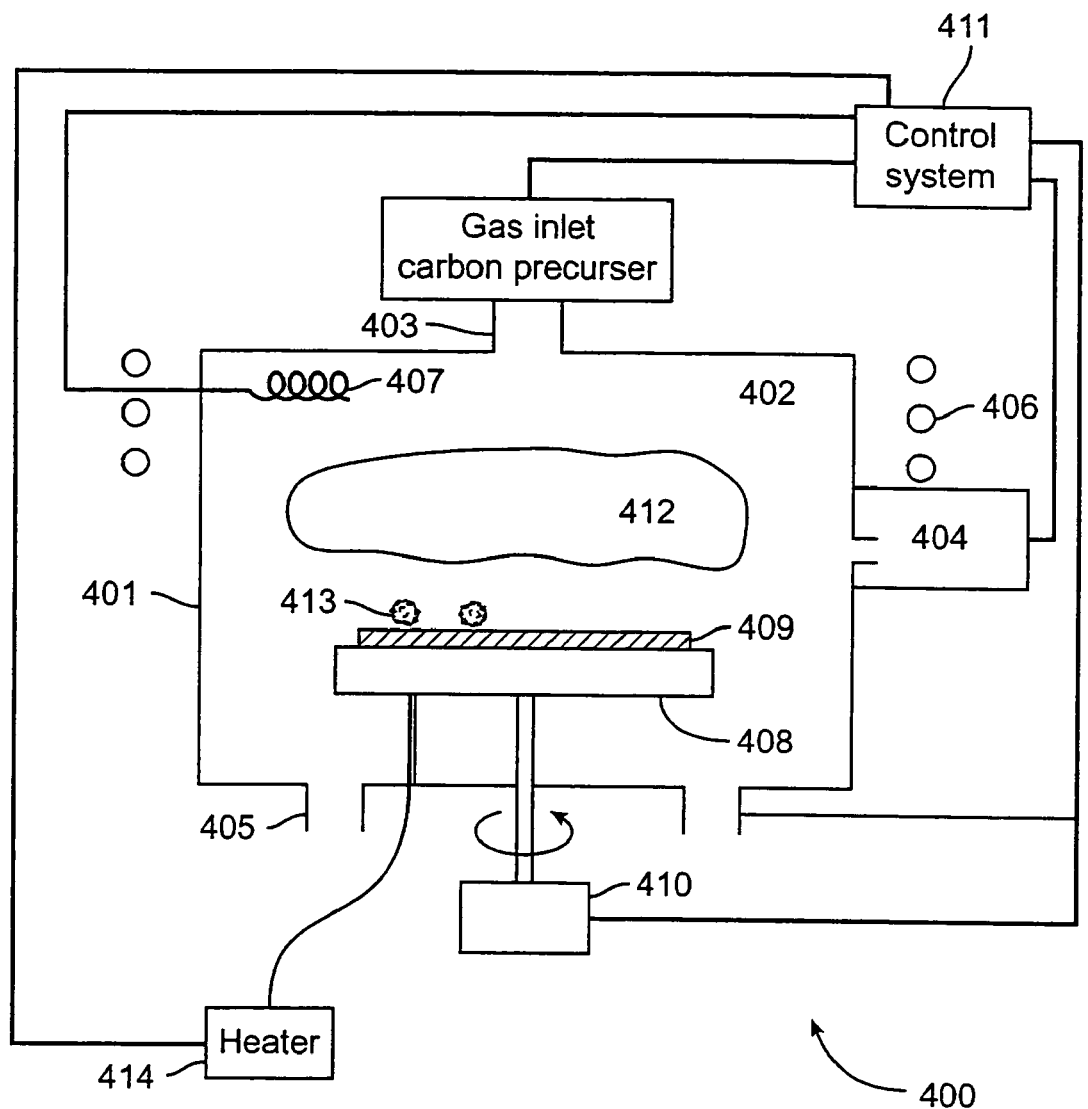
FIG. 4 illustrates an exemplary processing reactor in which a diamondoid-containing film may be synthesized using chemical vapor deposition (CVD) techniques, including the use of the diamondoids triamantane and higher to nucleate a film grown "conventionally" by plasma CVD techniques.

It is contemplated that a similar device may be used to sublime diamondoids into the gas phase such that they to may be introduced to a CVD reactor. An exemplary reactor is shown in generally at 400 in FIG. 4. A reactor 400 comprises reactor walls 401 enclosing a process space 402. A gas inlet tube 403 is used to introduce process gas into the process space 402, the process gas comprising methane, hydrogen, and optionally an inert gas such as argon. A diamondoid subliming or volatilizing device 404, similar to the quartz transpirator discussed above, may be used to volatilize and inject a diamondoid containing gas into the reactor 400. The volatilizer 404 may include a means for introducing a carrier gas such as hydrogen, nitrogen, argon, or an inert gas such as a noble gas other than argon, and it may contain other carbon precursor gases such as methane, ethane, or ethylene.

Consistent with conventional CVD reactors, the reactor 400 may have exhaust outlets 405 for removing process gases from the process space 402; an energy source for coupling energy into process space 402 (and striking a plasma from) process gases contained within process space 402; a filament 407 for converting molecular hydrogen to monoatomic hydrogen; a susceptor 408 onto which a diamondoid containing film 409 is grown; a means 410 for rotating the susceptor 408 for enhancing the $sp^3$-hybridized uniformity of the diamondoid-containing film 409; and a control system 411 for regulating and controlling the flow of gases through inlet 403, the amount of power coupled from source 406 into the processing space 402; and the amount of diamondoids injected into the processing space 402 the amount of process gases exhausted through exhaust ports 405; the atomization of hydrogen from filament 407; and the means 410 for rotating the susceptor 408. In an exemplary embodiment, the plasma energy source 406 comprises an induction coil such that power is coupled into process gases within processing space 402 to create a plasma 412.

A diamondoid precursor (which may be a triamantane or higher diamondoid) may be injected into reactor 400 according to embodiments of the present invention through the volatilizer 404, which serves to volatilize the diamondoids. A carrier gas such as methane or argon may be used to facilitate transfer of the diamondoids entrained in the carrier gas into the process space 402. The injection of such diamondoids may facilitate growth of a CVD grown diamond film 409 by allowing carbon atoms to be deposited at a rate of about 10 to 100 or more at a time, unlike conventional plasma CVD diamond techniques in which carbons are added to the growing film one atom at a time. Growth rates may be increased by at least two to three times and in some embodiments, growth rates may be increased by at least an order of magnitude.

It may be necessary, in some embodiments, for the injected methane and/or hydrogen gases to "fill in" diamond material between diamondoids, and/or "repair" regions of material that are "trapped" between the aggregates of diamondoids on the surface of the growing film 409. Hydrogen participates in the synthesis of diamond by PECVD techniques by stabilizing the $sp^3$ bond character of the growing diamond surface. As discussed in the reference cited above, A. Erdemir et al. teach that hydrogen also controls the size of the initial nuclei, dissolution of carbon and generation of condensable carbon radicals in the gas phase, abstraction of hydrogen from hydrocarbons attached to the surface of the growing diamond film, production of vacant sites where $sp^3$ bonded carbon precursors may be inserted. Hydrogen etches most of the double or $sp^2$ bonded carbon from the surface of the growing diamond film, and thus hinders the formation of graphitic and/or amorphous carbon. Hydrogen also etches away smaller diamond grains and suppresses nucleation. Consequently, CVD grown diamond films with sufficient hydrogen present leads to diamond coatings having primarily large grains with highly faceted surfaces. Such films may exhibit the surface roughness of about 10 percent of the film thickness. In the present embodiment, it may not be as necessary to stabilize the surface of the film, since carbons on the exterior of a deposited diamondoid are already $sp^3$ stabilized.

Diamondoids may act as carbon precursors for a CVD diamond film, meaning that each of the carbons of the diamondoids injected into processing space 402 are added to the diamond film in a substantially intact form. In addition to this role, diamondoids 413 injected into the reactor 400 from the volatilizer 404 may serve merely to nucleate a CVD diamond film grown according to conventional techniques. In such a case, the diamondoids 413 are entrained in a carrier gas, the latter which may comprise methane, hydrogen, and/or argon, and injected into the reactor 400 at the beginning of a deposition process to nucleate a diamond film that will grow from methane as a carbon precursor (and not diamondoid) in subsequent steps. In some embodiments, the selection of the particular isomer of a particular diamondoid may facilitate the growth of a diamond film having a desired crystalline orientation that may have been difficult to achieve under conventional circumstances. Alternatively, the introduction of a diamondoid nucleating agent into reactor 400 from volatilizer 404 may be used to facilitate an ultracrystalline morphology into the growing film for the purposes discussed above.

As described by D. M. Gruen in "Nucleation of ultrananocrystalline diamond films" in *Properties, Growth, and Applications of Diamond*, edited by M. H. Nazare and A. J. Neves (Inspec, Exeter, 2001), pp. 303-306, in order to obtain ultrananocrystalline film growth having a microstructure consisting of a 3-5 nanometer crystallite size, the nucleation rate has to increase from a conventional value of $10^4$ cm$^{-2}$ s$^{-1}$ to about $10^{10}$ cm$^{-2}$ s$^{-1}$. This $10^6$ order of magnitude increase in nucleation rate may be provided by the introduction of sublimed diamondoids into the reactor 400 at the beginning of a CVD deposition process.

It has been pointed out by W. Kulisch in "Deposition of Diamond-Like Superhard Materials," Section 4.2, *Nucleation of Diamond* (Springer, Berlin, 1999), that the nucleation of diamond is complicated by the fact that one must distinguish between carbide-forming substrates (e.g. Si and Mo) and non-carbide forming substrates (Ni and Pt). In the former case, the diffusion of carbon into the substrate leads to a carbide layer which acts as a barrier to further carbon diffusion, and an increased carbon concentration on the surface. The barrier is a necessary but not sufficient condition for the rapid formation of nuclei on the surface of the substrate. For non-carbide forming substrates, on the other hand, deposition begins with the formation of a graphitic, and generally greater carbon-like layer before any diamond nuclei can be observed. According to embodiments of the present invention, the injection of diamondoid containing gases into reactor 400 at the beginning of a CVD diamond process may render the reaction independent of the nature of the substrate, since the diamondoid particles acting as nuclei are so large and thermodynamically stable that diffusion of carbon into the substrate is not practical. In one embodiement, a method of nucleating the growth of a diamond film involves the injection of a triamantane diamondoid into the CVD reactor at the beginning of a deposition process. In another embodiment, diamondoid film growth is nucleated with a higher diamondoid, where the higher diamondoid may comprise tetramantane, pentamantane, hexamantane, heptamantane, octamantane, nonamantane, decamantane, and undecamantane, including combinations thereof and combinations with triamantane. Of course, the diamondoids mentioned above may be used to nucleate diamond films grown by other types of processes in other types of reactors, and these embodiments are not limited to chemical vapor deposition.

The weight of diamondoids and substituted diamondoids, as a function of the total weight of the CVD film (where the weight of the diamondoid functional groups are included in the diamondoid portion), may in one embodiment range from about 1 to 99.9 percent by weight. In another embodiment, the content of diamondoids and substituted diamondoids is about 10 to 99 percent by weight. In another embodiment, the proportion of diamondoids and substituted diamondoids in the CVD film relative to the total weight of the film is about 25 to 95 percent by weight.

In addition to techniques where diamondoids are used as precursors for CVD diamond film deposition and nucleation entities, diamondoids may also be incorporated into a film by self-assembly techniques. Diamondoids and their derivatives can undergo self-assembly in a variety of ways. For example, diamondoid-thiols may self-assemble on various metal surfaces, as illustrated generally in FIG. 5A, where a diamondoid monolayer 501 has self-assembled on a metal layer 502. The diamondoids comprising the monolayer 501 may be either lower diamondoids, higher diamondoids, or both. If the diamondoids of the monolayer 501 are lower diamondoids, they may be synthesized or isolated from a suitable feedstock. If the diamondoids comprising monolayer 501 are higher diamondoids, they may be isolated from a suitable feedstock when synthesis is not possible. These selected diamondoids can then be derivatized, in this example, to form a thiol-diamondoid 503. The thio-diamondoid derivative 503 can then self-assemble, and undergo partial or complete orientation in the process, by bonding to the metal surface 502. In one embodiment, the metal surface 502 comprises gold or a gold alloy. Alternatively, the diamondoid layer 501 may self-assemble on the metal layer 502 through alkyl sulfide groups, an example of which may be represented by the sequence "metal layer 502-S—$C_{12}H_{24}$-diamondoid," or "metal layer 502-S-R-diamondoid," where R represents an alkyl group.

In an alternative embodiment, a diamondoid layer may self-assemble by hydrogen bonding to either a substrate or to some other layer, including another diamondoid-containing layer, or a non-diamondoid containing layer. In the exemplary embodiment illustrated in FIG. 5A, the diamondoid layer 501 has hydrogen-bonded to a non-diamondoid layer 504, such that the diamondoid layer 501 is sandwiched between the non-diamondoid layer 504 and the metal layer 502. It will be apparent to those skilled in the art that the hydrogen-bonding of the diamondoid layer 501 to the non-diamondoid layer 504 does not require the derivatization of the diamondoid layer 501 if hydrogens 505 on the diamondoid layer 501 are bonding to hydroxyl groups 506 on the non-diamondoid layer 504. Hydrogen bonding could occur, however, between hydroxyl groups on the diamondoids 503 and hydrogens on the non-diamondoid layer 504, in which case the diamondoids 503 might be derivatized.

Figure 5A:
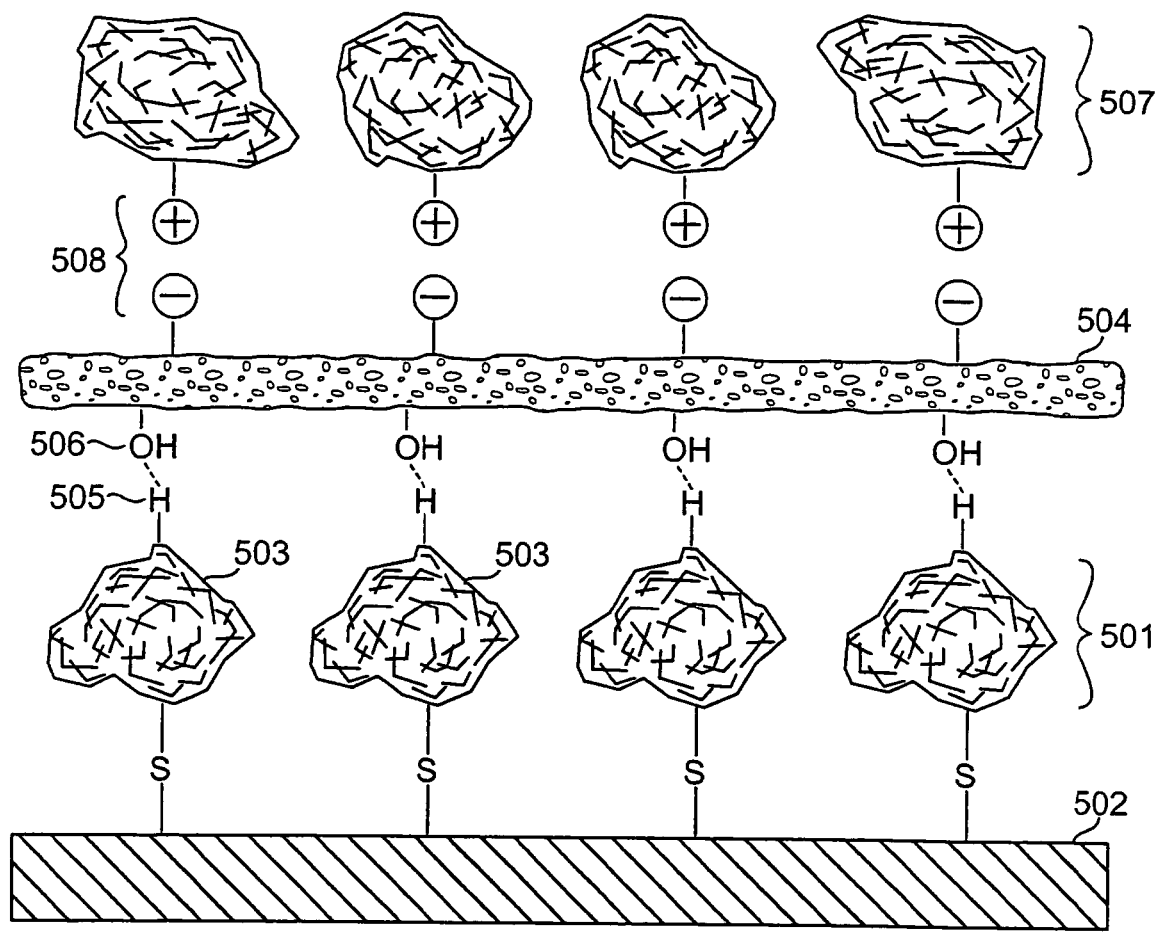
FIG. 5A illustrates an exemplary diamondoid-containing film that may be fabricated by self-assembly techniques.

In addition to a chemically based self-assembly, a diamondoid or diamondoid-containing layer could self-assemble through electrostatic interactions. This possibility is illustrated at the top of FIG. 5A, where a diamondoid layer 507 has electrostatically self-aligned on the non-diamondoid layer 504 through electrostatic interactions 508. In this example the diamondoid layer 507 has positive charges and the substrate on which it is aligning has negative charges, but of course this could be reversed, and there could be a mixture of positive and negative charges on each layer.

In addition to the examples cited above, a derivatized diamondoid may self-assemble on a layer having a plurality of functional groups that are complimentary to the derivatizing groups on the diamondoids. Likewise, derivatized diamondoids may polymerize in a self-assemblying fashion given the complementary nature of functional groups. In other words, monomers may be induced to self-assemble into polymers. The formation of polymers, like the self-assembling chemical reactions described above, is a method of locking diamondoids into desired orientations with desired thicknesses. The polymers can be synthesized directly on a desired substrate.

Formation of molecular crystals is another means of inducing diamondoids and their derivatives to self-assemble. Once a particular diamondoid has been isolated and purified (and derivatized if desired), crystals can be grown by slowly evaporating diamondoid solvents such as cyclohexane. By varying conditions such as the temperature, the solvent composition and the speed of solvent evaporation, the size of the individual crystals can be controlled. They can range in size from nanometers to centimeters, depending on the processing conditions. The resulting self-assembled crystals can orient the diamondoid molecules in a preferred direction or set of directions. Self-assembled crystals may be grown directly on a desired substrate.

Figure 5B:
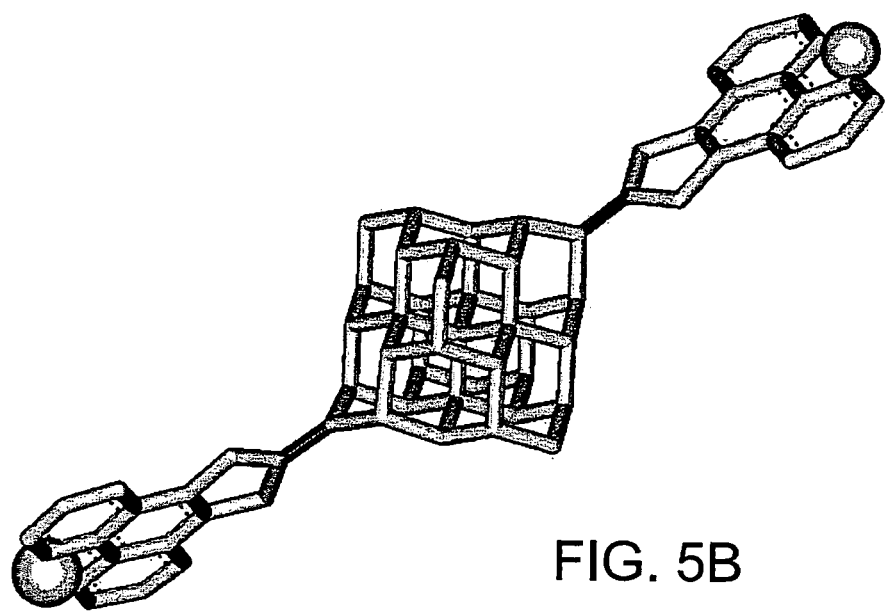
FIG. 5B illustrates a chelate-derived linker comprising a decamantane; the linker which may comprise a linear bridging unit for connecting molecular electronic and electro-optical devices.
Figure 5C:
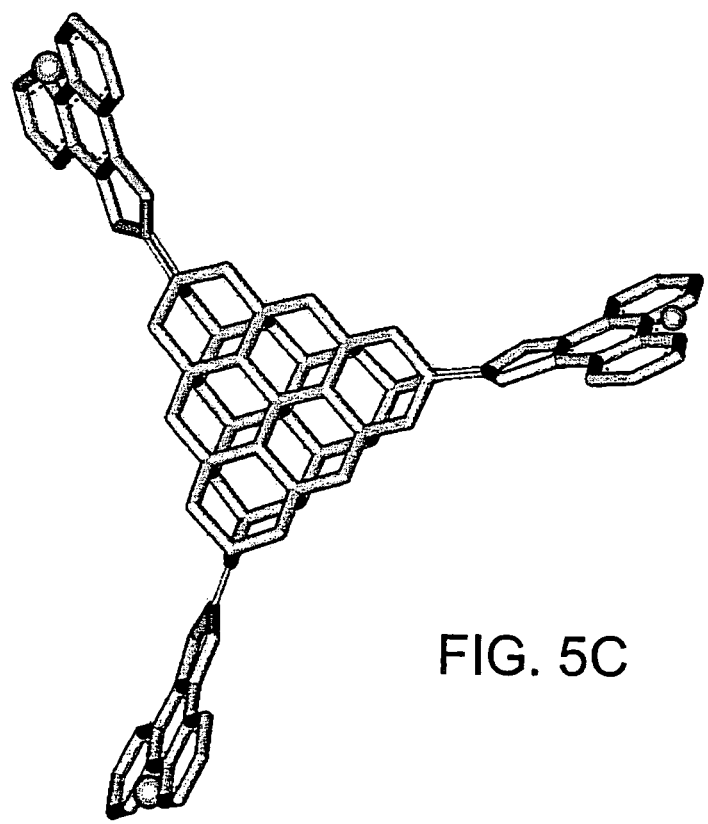
FIG. 5C illustrates a chelate-derived linker comprising a nonamantane; the linker may comprise a two-dimensional bridging unit for connecting molecular electronic and electro-optical devices.

Higher diamondoid derivatives containing two or more chelation sites can be used to construct nanometer-sized linker units that self-assemble in the presence of appropriate metal ions to form long chains of alternating metal ion and linker subunits. An example is shown in FIG. 5B, in which [1231241(2)3] decamantane functions as a linear linker unit. In FIG. 5C, [121(2)32(1)3] nonamantane functions as a 2-dimensional linker unit. Linear linkers using only adamantane have been described by J. W. Steed et al. in "Supermolecular Chemistry," (Wiley, New York, 2001), pp. 581-583. Various three-dimensional self-assembling units are possible given the wide range of higher diamondoid structures. Additionally, this approach may be used to design linker units which self-assemble into desired, predetermined arrays.

The weight of diamondoids and substituted diamondoids that may be incorporated into a self-assembled film, as a function of the total weight of the film (where the weight of the functional groups are included in the diamondoid portion) may in one embodiment range from about 1 to 99.99 percent by weight. In another embodiment, the content of diamondoids and substituted diamondoids is about 10 to 98 percent by weight. In another embodiment, the proportion of diamondoids and substituted diamondoids in the ceramic is about 25 to 98 percent by weight of the total weight of the self-assembled film.

Applications of Diamondoid-Containing Materials to Microelectronics

These applications include microelectronics packaging, passivation films for integrated circuit devices (ICs), low-k dielectric layers in multilevel interconnects, thermally conductive films, including adhesive films, thermoelectric cooling devices, and field emission cathodes.

The process of preparing an integrated circuit (IC) chip for use is called packaging. An overview of IC packaging has been presented by T. Tachikawa in a chapter entitled "Assembly and Packaging," *ULSI Technology* (McGraw Hill, New York, 1996), pp. 530-586. The purpose of IC packaging is to provide electrical connections for the chip, mechanical environmental protection, as well as a conduit for dissipating heat that evolves as the chip is operated. Integrated circuit devices include memory, logic, and microprocessing devices. Packaging devices include hermetic-ceramic and plastic packages. Each have their own level of power dissipation, and pose their own requirements in terms of the thermal path to dissipate heat. Integrated circuit clock speeds and power densities are increasing, and since package sizes are simultaneously decreasing, thermal dissipation becomes a long-term packaging reliability issue. The heat generated by an IC is proportional to its computing power, which is the product of the number of transistors in the IC and their clock frequencies. Although the computing power of a typical IC has increased significantly in recent years, design rules such as the operating temperature have not substantially changed, placing demands on the methods by which dissipated heat is removed.

As discussed by T. Tachikawa, chip interconnection typically consists of two steps. In a first step, the back of the chip is mechanically bonded to an appropriate medium, such as a ceramic substrate or the paddle of a metal lead frame. Chip bonding provides, among other things, a thermal path for heat to be dissipated from the chip to the substrate medium. In a second step, the bond pads on the circuit side of the chip are electrically connected to the package by wire bonding, typically using fine metal wires of gold or aluminum.

As the amount of heat generated by the integrated circuit increases, so too does the junction temperature of the components transistors in a proportional manner. The failure rate of the semiconducting device is in general related to the junction temperature at which the device is operated. It is generally known to provide a heat spreader or heat sink in order to transfer the heat generated by the device away from the device and into either the surrounding air or the substrate, thus reducing transistor junction temperatures. Heat sinks are typically constructed from materials having high thermal conductivity, such as copper, aluminum, BeO, and diamond, although other material properties are taken into consideration, such as density, and thermal expansion coefficient. Since CVD diamond has a thermal conductivity (up to 2500 W/mK) three to five times greater than that of copper (about 391 W/mK) a thermal expansion coefficient similar to that the Si and GaAs, and high electrical resistivity, CVD diamond offers an attractive alternative to traditional metallic heat spreading materials, particularly when formed such that they facilitate transfer of heat from an integrated circuit to a conventional metallic heat sink/substrate.

Figure 6A:
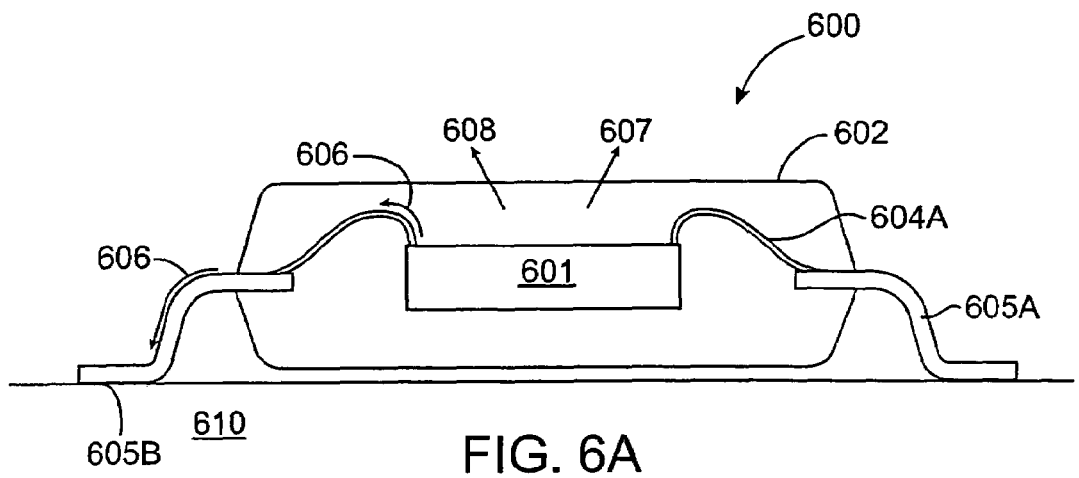
FIGS. 6A-C illustrate an exemplary heat transfer application, in which a thermally-conducting film and/or fiber facilitates heat dissipation from an integrated circuit (IC) to a conventional heat sink.

An exemplary model of a packaged integrated chip is shown generally at 600 in FIG. 6A to illustrate the processes by which heat is dissipated from an integrated circuit, where a chip 601 is supported by a frame (not shown) within a plastic package 602. Metallic bond wires 604A, 604B connect the chip to a lead 605A, 605B, respectively. Dissipated heat is conducted away from the chip by conductive heat transfer along pathways 606 (according to Fourier's equation), by convection 607 (Newton's cooling law), and by radiation 608 (following the Stefan-Boltzmann law).

In one embodiment of the present invention, a diamondoid containing heat transfer film 620 is positioned adjacent to integrated circuit chip 601 and a heat sink 610 positioned inside the package 625. By providing heat transfer film 620, heat from the integrated circuit 601 may diffuse along a pathway 621 in a substantially direct route into the heat sink material 610, or alternatively, may be conducted along heat transfer path 622 into the heat sink at 623. This provides an additional pathway for the removal of heat. By providing heat transfer film 620, and pathway 622, heat may be dispersed into heat sink 610 at positions 623 that are laterally displaced from the integrated circuit chip 601, and in this manner, heat removal from integrated circuit 601 is facilitated.

In another embodiment of the present invention, there may not be sufficient room within or immediately adjacent to the integrated circuit chip 601 for a heat sink. In FIG. 6C, a larger heat sink 630 is positioned outside the package 635. In this embodiment, heat pipes or heat conduits 631, 632 may be used to conduct heat away from the chip to a heat sink located remotely from the package. The heat conduits may be in fiber form, and may be inserted into the integrated circuit chip itself at locations 633, 634, or they may communicate with thermal vias (not shown) within the chip. The heat conducting conduits may be flexible fibers, or rigid rods. There may be from about 1 to 100 of the heat conducting fibers or rods.

Figure 6B:
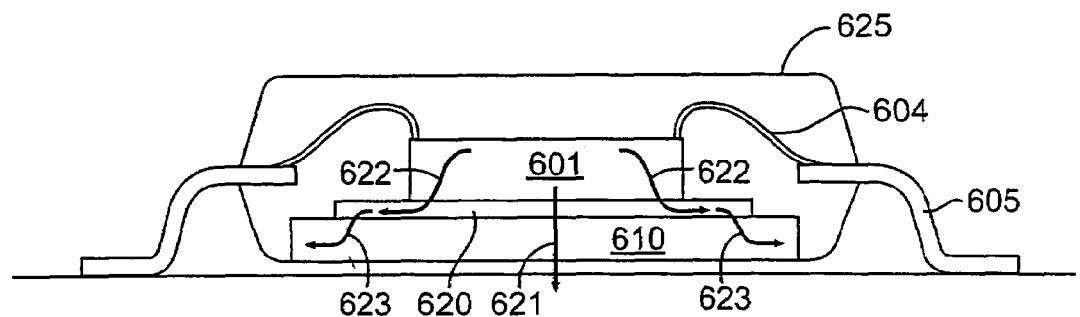
Figure 6C:
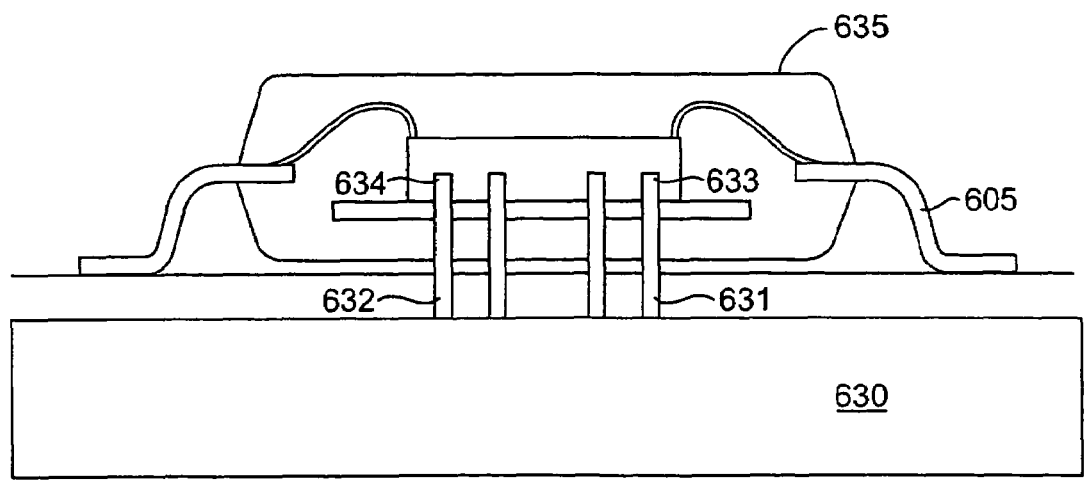

The heat transfer film 620 of FIG. 6B, and heat conduits 630 of FIG. 6C may comprise any of the diamondoid-containing materials discussed above, such as a polymerized diamondoid film, a diamondoid-containing ceramic and/or ceramic composite, a CVD deposited diamondoid-containing film, a CVD diamond film nucleated by diamondoids, or a diamondoid-containing film deposited by self-assembly techniques. According to one embodiment of the present invention, the heat transfer film 620 comprises a diamondoid-containing polymer similar to that depicted in FIG. 2A, particularly where diamondoid 201 is connected to an adjacent diamondoid 202 through either covalent linkage 204 or covalent linkage 205. The covalent linkage 204 bonds carbons that are members of the diamondoid nucleus itself; alternatively, the covalent linkage 205 is a bond in which the constituent carbons of the bond comprise attachments or substituents to the diamondoid nuclei they are connecting.

It will be recognized by those skills in the art that since diamondoids themselves are hydrocarbons, heat transfer within a van der Waals solid will be less efficient than through a polymer having a continuous network of C—C bonds. The heat transfer film 620 may be very thin, comprising a minor layer of diamondoids such that the heat flow is through just the diameter of a single diamondoid. In this manner, as above, a continuous network of C—C bonds is provided.

Figure 7A:
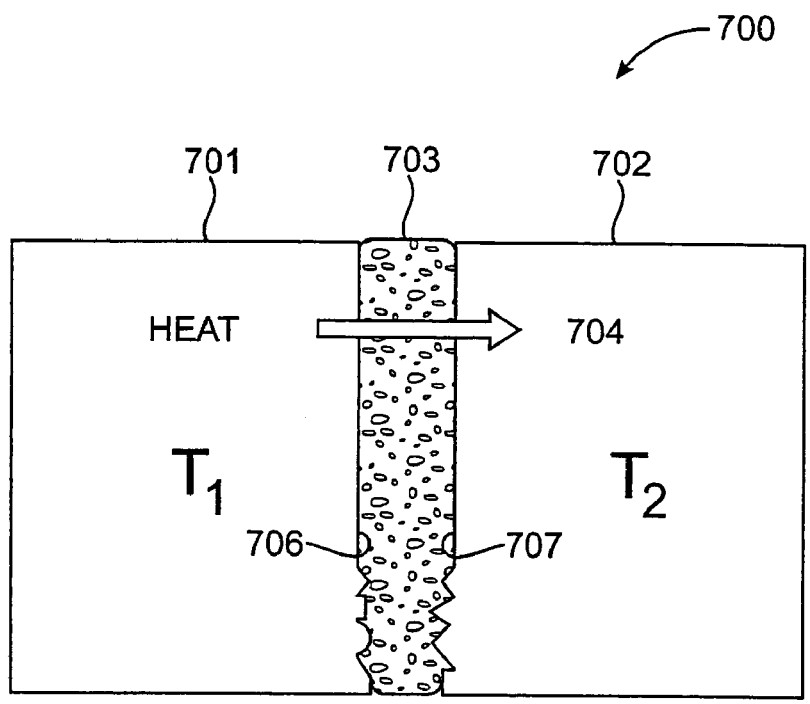
FIGS. 7A-B illustrate an exemplary heat transfer application in which a diamondoid-containing material is used as a thermally-conductive film, in this case adhering two objects together, the two objects being maintained at two different temperatures in a situation where rapid heat flow between the two objects is desired.
Figure 7B:
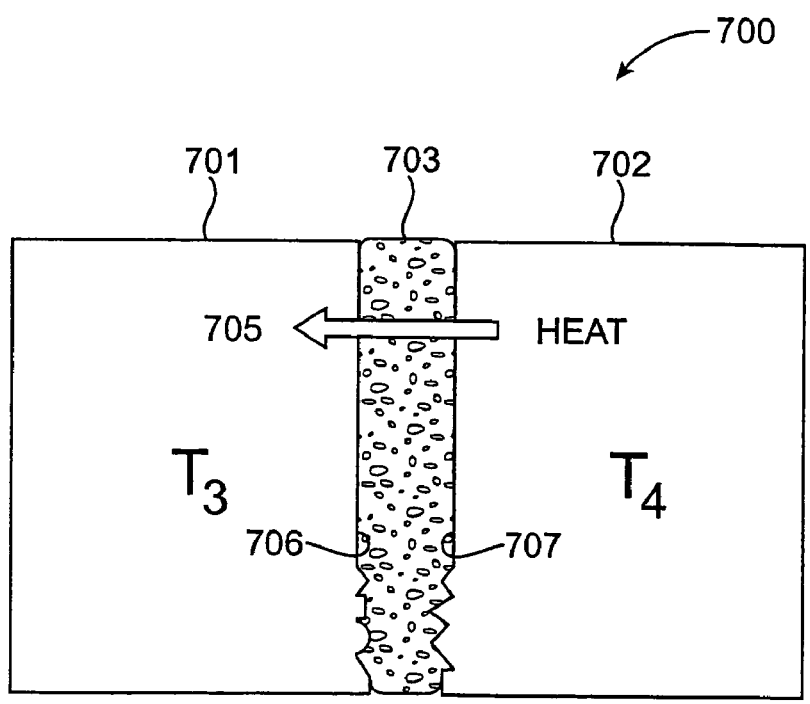

Diamondoids may be used as thermally-conducting films in other microelectronics applications, such as an adhesive film, or as an intermediate heat transfer film as part of a thermoelectric cooling device. An exemplary application of a thermally conducting adhesive film is shown generally with device 700 in FIGS. 7A-B. The device 700 in FIG. 7A comprises an object 701 at a temperature $T_1$, adhesively connected to an object 702 at temperature $T_2$, the connection means comprising a thermally-conducting adhesive film 703. In this example, it is desired to adhere the object 701 to the object 702, with a minimum of resistance of heat flow between the two bodies. At one time, the temperature $T_1$ may be for example greater than the temperature $T_2$, and in this case, heat will be allowed to flow flow rapidly from the object 701 to the object 702, an interaction 704, with a minimum of thermal resistance.

As this exemplary device 700 is being operated, the temperatures of the two bodies may change virtually instantaneously, such that at a later time the temperature of the body 702 is $T_4$ and the temperature of the body 701 is $T_3$, where $T_4$ is greater than $T_3$. As the device is being operated into the second configuration of FIG. 7B, it may still be desirable to adhere to the object 701 to the body 702 with a substantially minimal resistance to heat flow. In this case, the thermally conducting films 703 allows heat to flow in an reverse direction 705, from the object 702 back to the object 701.

The thermally-conducting adhesive film 703 may comprise any of the material forms discussed above, such as as a polymerized diamondoid film, a diamondoid-containing ceramic and/or ceramic composite, a CVD deposited diamondoid-containing film, a CVD diamond film nucleated by diamondoids, or a diamondoid-containing film deposited by self-assembly techniques. In a preferred embodiment, however, the thermally-conducting adhesive film 703 is a diamondoid-containing polymeric film, in which substituent groups are attached either to the diamondoid nuclei themselves, or to other portions of the polymer, such that adhesion is facilitated. An exemplary functional group that may be incorporated into a diamondoid-containing film to facilitate adhesion is a carboxyl group. Such a device configuration is contemplated to be useful in a variety of applications in microelectronics and nanotechnology. Of course, it will be appreciated by those skilled in the art that the surface 706 of body 701 and surface 707 of body 702, in other words, the two surfaces being "glued" together, do not have to comprise smooth surfaces 706, 707, and in some embodiments of the present invention, a flexible diamondoid-containing adhesive film is well-suited to adhere irregularly-shaped materials one to another, such as the rough surfaces depicted at 708, 709.

An additional exemplary use of a diamondoid-containing material having thermally conductive and electrically insulating properties is a thermoelectric cooling device. It is known in the art that CMOS logic devices operate significantly faster at low temperatures. Efforts have been made in the past to reduce the temperature at which a microelectronic device is operated, including methods that include thermoelectric devices.

Figure 8:
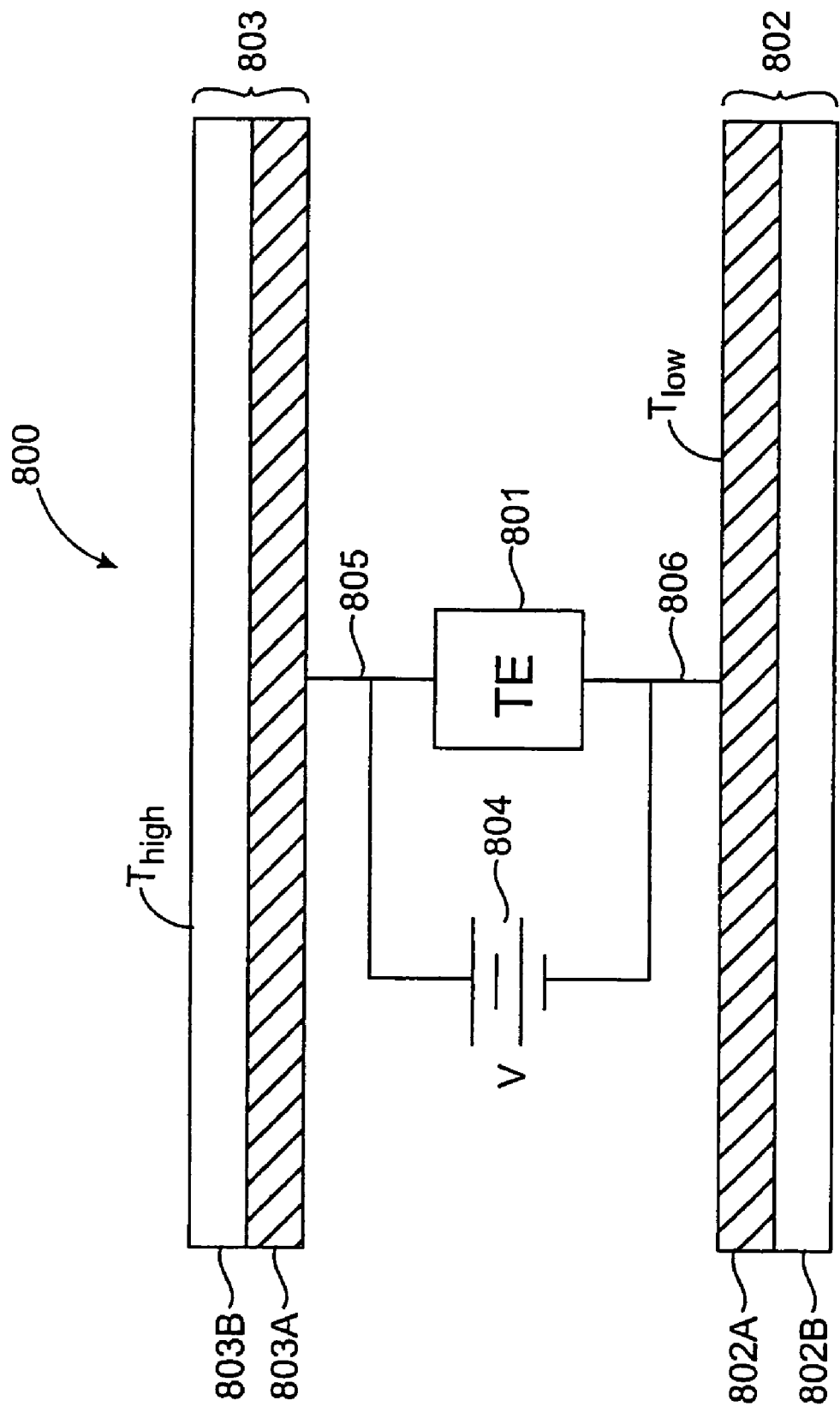
FIG. 8 illustrates an exemplary heat transfer application, in which a diamondoid-containing material is used in a thermoelectric cooler (or Peltier-based device)

An exemplary microelectronics application in which a film that is both thermally conducting and electrically insulating may be useful is the thermoelectric device shown generally at 800 in FIG. 8. The thermoelectric device 800 has an element 801 whose purpose is to pump heat from a cold substrate 802 to a hot substrate 803. The thermoelectric element 801 operates in a conventional manner by supplying DC power from a supply 804 to provide a potential difference across the junction of two dissimilar materials, which may be semiconductors. In FIG. 8, the potential is applied between points 805 and 806. The temperature of substrate 803 is at a high temperature, for example, $T_{high}$, whereas the temperature of substrate 802 is at a low-temperature, for example, $T_{low}$. The purpose of the thermoelectric device 801 is to remove heat from the substrate at the low-temperature 802 in a thermally "uphill" manner to substrate 803.

The thermal conductivity of the thermoelectric device 800 depends in part upon the characteristics of the element 801, as well as the thermal conductivites of substrates 802 and 803. Any resistance to the transfer of heat from substrate 802 to substrate 803 reduces the efficiency at which the device 800 operates. According to one embodiment of the present invention, the efficiency of the device 800 may be enhanced by providing a thermally conducting layer 802A adjacent to a heat sink layer 802B. Likewise, the substrate 803 may comprise a thermally conducting layer 803A positioned adjacent to a heat sink layer 803B. The enhanced level of thermal conductivity of the layers 802A and 803A reduces the thermal resistance for removing heat from the system via the substrates 802 and 803, respectively. In an embodiment of the present invention, the thermally-conducting layers 802A and 803A may comprise any of the material discussed above, such as as a polymerized diamondoid film, a diamondoid-containing ceramic and/or ceramic composite, a CVD deposited diamondoid-containing film, a CVD diamond film nucleated by diamondoids, or a diamondoid-containing film deposited by self-assembly techniques. In a preferred embodiment, however, the thermally-conducting layers 802A and 803A comprise a diamondoid-containing polymer film or a diamondoid-containing ceramic.

Referring again to FIG. 8, thermally conducting layers 802A and 803A are electrically insulating as well in order to provide electrical isolation of the thermoelectric device 800. It will be obvious to those skilled in the art that if the layers 802A and 803A are not sufficiently electrically insulating, then the potential difference across element 801 attempted by the supply 804 may be less than not desired, as well as unreliable or nonuniform. The electrical insulation and thermal conduction properties of diamondoid films suggest a utility in microelectronic applications such as thermoelectric device 800 where both properties are simultaneously desired.

In one embodiment of the present invention, the thermal conductivity of the material used in the above mentioned applications is at least 200 W/m K. In a preferred embodiment of the invention, the thermal conductivity of the material is at least 500 W/m K. In an even more preferred embodiment of the present invention, the thermal conductivity of the material is at least 1,000 W/m K.

An example of an application in which electrical insulation of a diamondoid-containing material is the property of greatest interest relates to so-called back-end processing of an integrated circuit device. As transistor sizes in ultra large-scale integrated circuits are decreased, it is desirable to reduce the capacitance of the metal interconnection lines to each other to minimize the delays of electrical signals conducted by the metal interconnection lines, as well as to reduce "crosstalk" between the lines. This permits the integrated circuit to maintain or possibly even increase clock speed as the size of the component transistors are reduced.

One method for reducing the capacitance between interconnection lines is to deposit a polymeric or other insulating material on the integrated circuit chip between the metal interconnection lines where the polymeric or insulating material has a lower dielectric constant (k) then the conventionally used silicon dioxide ($SiO_2$). Silicon dioxide has a dielectric constant of about 3.9 to 4.0. Efforts have been made to replace silicon dioxide with a material having a dielectric constant lower than about 4.0 and these materials include, for example, the fluorinated oxides which have a dielectric constant of about 3.5. Fluorinated oxides are sometimes described by the acronym FSG, or by the symbols SiOF and $F_xSiO_y$. There are a variety of other silicon-containing low-k materials that are not a fluorinated version of the conventionally used silicon dioxide. Carbon-doped glass, or SiOC, has a dielectric constant of about 2.5 to 3.1. The polysiloxanes HSQ, hydrogen silsesquioxane (HSi $O_{3/2})_n$, and MSSQ, methyl silsesquioxane ($CH_3SiO_{1.5})_n$ have dielectric constants in the range 2.3 to 3.0. These materials are sometimes referred to as spin-on dielectrics (SOD's), or flowable oxides FOx (Dow Corning). Finally, there are low-k dielectric materials that cannot contain silicon, and in fact are either purely organic or substantially organic. Fluorinated amorphous carbon (FLAC, or α-CF), has a dielectric constant in the range 2.3 to 2.7. Polymeric materials include fluorinated poly(arylene ether) (FLARE, Allied Signal), fluorinated polyimide (DuPont), parylene, polyphenylquinoxaline (PPQ), benzocyclobutene (BCB), and the like. Members of this latter group of purely or substantially organic materials have dielectric constants in the range of about 2.0 to 3.0.

During back-end processing, that is to say, when the interconnection system is constructed, a problem may occur when silicon based low-k dielectric materials are etched in the presence of oxygen. Such low-k materials containing silicon may be more sensitive to oxygen than the purely organic low-k materials. Oxidation of either HSQ or MSSQ converts Si—H bonds to Si—OH bonds, which causes the material to absorb moisture, and experience an increase in the dielectric constant. Thus, it is advantageous to provide a low-k material for back end processing that is substantially organic and that does not contain silicon as an element.

In an article written by E. Korczynski entitled "Low-k dielectric costs for dual-damascene integration," *Solid State Technology*, May 1999, pp. 43-51, it is pointed out that in a fluorinated amorphous carbon film, variously called FLAC, α-CF, and $CF_x$, which may be produced by conventional CVD techniques, that by controlling the fluorine to carbon ratio in the precursor gases, as well as plasma parameters, the formation of electrically conductive C═C bonds having an $sp^2$ hybridization may be eliminated, leading to a film with a lower (and therefore more desirable) dielectric constant. Furthermore, it is known in the art to provide a porous version of a low-k dielectric material in order to achieve a dielectric constant less than about 2 (polytetrafluoroethylene, with a dielectric constant of about 2.1, is about the best achieved so far). This is because a porous dielectric material may be thought of as a composite where the dielectric constant of the air gaps (1.0) reduces the average and the overall dielectric constant of the material as a whole. Thus, it is desirable to provide a material for use in back-end integrated circuit processing that has 1) porosity in the form of air gaps, 2) strong and rigid mechanical properties, 3) predominantly $sp^3$ carbon carbon bonding, and optionally 4) some degree of fluorine content.

In one embodiment of the present invention, a diamondoid containing material may be used for the low-k layers associated with integrated circuit multilevel interconnection schemes. An exemplary integrated circuit for which a diamondoid-containing low-k dielectric layer is suitable is shown schematically in FIG. 9A. This exemplary integrated circuit is a member of the CMOS technology family (complementary metal oxide semiconductor), where an NMOS (N-type metal oxide semiconductor) device is shown on the right and a PMOS (P-type metal oxide semiconductor) device is shown on the left. A boron implanted p-type silicon substrate 901 has a PMOS transistor shown generally at 902 fabricated and in n-well 903 of the silicon substrate 901. An NMOS transistor 904 has been fabricated in a p-well 905.

After the transistors have been fabricated on (actually in) the surface of the silicon substrate 901, "back-end processing" occurs to construct the interconnection system that connects individual transistors, such as the CMOS transistor 902 and the NMOS transistor 904. Two levels of metal interconnect lines are shown: the first level at 906 and the second level at 907. Metallic vias 908 and 909 serve to vertically connect the upper interconnection level 907 with the lower interconnection level 906. As it will be appreciated by those skilled in the art, a dielectric layer or electrically insulating layer will be deposited to isolate the interconnect lines located at any one level from one another, as well as from interconnection lines or transistor electrode leads from one another and from interconnection lines. For example, low-k dielectric layer 910 insulates interconnection lines at the 906 level from the leads of the 902, 904 transistors. Low-k dielectric layer 911 insulates interconnection lines located at the 906 level from one another, as well as from the interconnect lines located at the 907 level. Additionally, the low-k dielectric layer 911 isolates the vias 908, 909 from one another.

According to embodiments of the present invention, the low-k dielectric layers 910, 911 may comprise any of the diamondoid containing materials discussed above, including a polymerized diamondoid film, a diamondoid-containing ceramic and/or ceramic composite, a CVD deposited diamondoid-containing film, a CVD diamond film nucleated by diamondoids, or a diamondoid-containing film deposited by self-assembly techniques. In a preferred embodiment, however, the low-k dielectric layers 910, 911 comprise a diamondoid-containing polymeric film, which may be a polymer such as a polyamide or a polyaryl ether. In this embodiment, the diamondoid-polyimide film of FIG. 2C may be used. The polyimide portion of the copolymer illustrated in FIG. 2C may be a fluorinated polyimide, and the diamondoid containing portion of the polymer may contain fluorine substituents. Additionally, a diamondoid-containing material which is suitable for low-k dielectric layers 910, 911 may contain air gaps 239 for reducing the overall dielectric constant of the material. As discussed previously, these air gaps 239 may be formed by the steric hindrance created with a large number of diamondoid groups spaced closely together either within the main chain of the polymer or present as side groups on the main chain of the polymer. The low-k dielectric layers 910, 911 may be deposited by conventional spin coating techniques, or by CVD methods. In some embodiments, ether linkages such as those depicted at reference numeral 234, 235 may be desirable to impact flexibility into the main chain, and facilitate the processing of the layer.

According to embodiments of the present invention, the low-k dielectric layers 910, 911 has a dielectric constant of less than about 4. In a preferred embodiment of the present invention, the dielectric constant of the material is less than about 3. In an even more preferred embodiment of the present invention, the dielectric constant of the material is less than about two.

Figure 9:
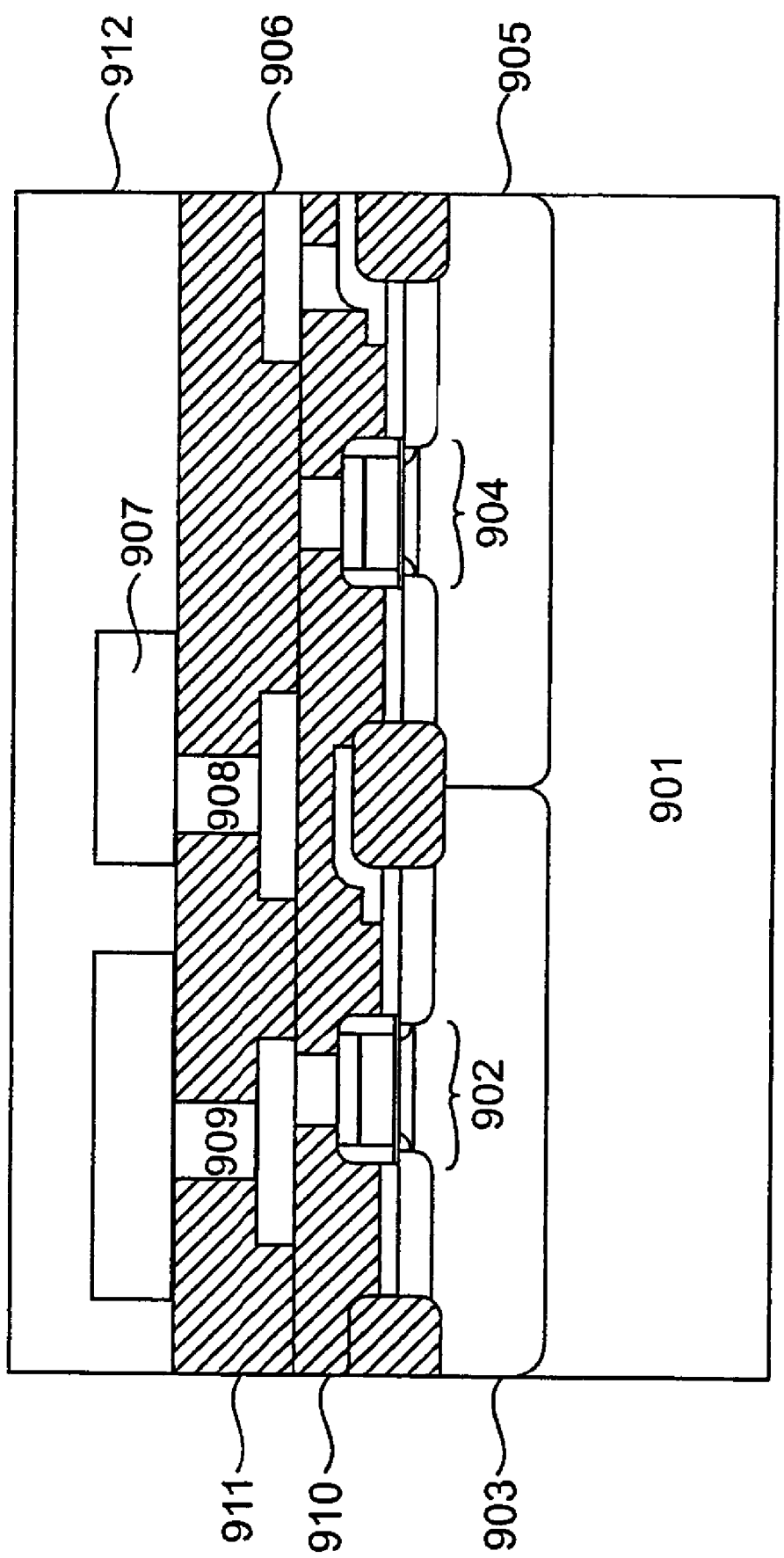
FIG. 9 is a schematic a cross-section of a typical integrated circuit, in this case a complementary metal oxide semiconductor (CMOS) device, illustrating where diamondoid-containing materials may be used as low-k dielectric layers in back-end multilevel interconnection processing, and as passivation layers protecting the top surface of the IC.

Integrated circuits such as those shown schematically in FIG. 9 may have a top passivation layer 912 that serves to mechanically protect the chip from environmental stresses and destructive conditions. In another embodiment of the present invention, the passivation layer 912 may comprise a diamondoid-containing material of the types discussed above, including a polymerized diamondoid film, a diamondoid-containing ceramic and/or ceramic composite, a CVD deposited diamondoid-containing film, a CVD diamond film nucleated by diamondoids, or a diamondoid-containing film deposited by self-assembly techniques. The diamondoid comprising the IC passivation layer may comprise a derivatized or underivatized diamondoid, and it may be either a higher or lower diamondoid, and/or combinations thereof. If the diamondoid of the passivation layer comprises a higher diamondoid, that diamondoid may be selected from the group consisting of tetramantane, pentamantane, hexamantane, heptamantane, octamantane, nonamantane, decamantane, and undecamantane.

In an alternative embodiment, the diamondoid-containing materials discussed above may be used in the dielectric layer of a capacitor, specifically, a capacitor for a static and/or dynamic random access memory (SRAM and DRAM, respectively). The capacitor will generally be configured as a first and second electrodes with the dielectric layer positioned between the electrodes. In one embodiment, the diamondoid of the diamondoid-containing capacitor dielectric material comprises a derivatized diamondoid; in another embodiment the diamondoid may be underivatized. The diamondoid may be a higher diamondoid or a lower diamondoid, or combinations thereof. If the capacitor dielectric layer comprises a higher diamondoid, the higher diamondoid may be tetramantane, pentamantane, hexamantane, heptamantane, octamantane, nonamantane, decamantane, or undecamantane, and combinations thereof.

In a final embodiment of the present invention, a diamondoid or diamondoid containing material is utilized as a cold cathode filament in a field emission device suitable for use, among other places, in flat panel displays. The unique properties of a diamondoid make this possible. These properties include the negative electron affinity of a hydrogenated diamond surface, in conjunction with the small size of a typical higher diamondoid molecule. The latter presents striking electronic features in the sense that the diamond material in the center of the diamondoid comprises high purity diamond single crystal, with the existence of significantly different electronic states at the surface of the diamondoid. These surface states may make possible very long diffusion lengths for conduction band electrons.

In a chapter entitled "Novel Cold Cathode Materials," in *Vacuum Micro-electronics* (Wiley, New York, 2001), pp. 247-287, written by W. Zhu et al., the current requirements for a microtip field emitter array are given, as well as the properties an improved field emission cathode are expected to deliver. Perhaps the most difficult problem presented by a conventional field emission cathode is the high voltage that must be applied to the device in order to extract electrons from the filament. Zhu et al. report a typical control voltage for microtip field emitter array of about 50-100 volts because of the high work function of the material typically comprising a field emission cathode. Diamonds in general, and in particular a hydrogenated diamond surface, offer a unique solution to this problem because of the fact that a diamond surface displays an electron affinity that is negative.

The electron affinity of the material is a function of electronic states at the surface of the material. When a diamond surface is passivated with hydrogen, that is to say, each of the carbon atoms on the surface are $sp^3$-hybridized, i.e., bonded to hydrogen atoms, the electron affinity of that hydrogenated diamond surface surface can become negative. The remarkable consequence of a surface having a negative electron affinity is that the energy barrier to an electron attempting to escape the material is energetically favorable and in a "downhill" direction. Diamond is the only known material to have a negative electron affinity in air.

In more specific terms, the electron affinity $\chi$ of a material is negative, where $\chi$ is defined to be the energy required to excite an electron from an electronic state at the minimum of the conduction band to the energy level of a vacuum. For most semiconductors, the minimum of the conduction band is below that of the vacuum level, so that the electron affinity of that material is positive. Electrons in the conduction band of such a material are bound to the semiconductor by an energy that is equal to the the electron affinity, and this energy must be supplied to the semiconductor to excite and electron from the surface of that material.

It should be noted that a field emission cathode comprising a diamond filament may suffer from an inherent property: while electrons in the conduction band are easily ejected into the vacuum level, exciting electrons from the valence band into the conduction band to make them available for field emission may be problematic. This is because of the wide bandgap of diamond. In a normal situation, few electrons are able to traverse the bandgap, in other words, move from electronic states in the valence band to electronic states in the conduction band. Thus, diamond is generally thought to be unable to sustain electron emission because of its insulating nature. To reiterate, although electrons may easily escape into the vacuum from the surface of a hydrogenated diamond film, due to the negative electron affinity of that surface, the problem is that there are no readily available mechanisms by which electrons may be excited from the bulk into electronic surface states.

There may be several ways to circumvent this problem. Observations of electron emission from diamond surfaces have either: 1) a high defect density, such as a relatively large inclusion of elemental nitrogen, or 2) an unusual microstructure including vapor-deposited islands or a film having a nanocrystalline morphology. They can also demonstrate quantum mechanically tunneling. It is known in the art that diamond materials with small grain sizes and high defect densities generally emit electrons more easily than diamond materials with large crystalline sizes and low defect defect concentrations. It has been reported (see the Zhu reference above) that outstanding emission properties are seen in ultrafine diamond powders containing crystallites having sizes in the range of 1 to 20 nm. Emission of electrons has been found to originate from sites that are associated with defect structures in diamond, rather than sharp features associated with the surface, and that compared with conventional silicon or metal microtip emitters, diamond emitters show lower threshold fields, improved emission stability, and robustness and vacuum environments.

According to embodiments of the present invention, a field emission cathode comprises a diamondoid, a derivatized diamondoid, a polymerized diamondoid, and all or any of the other diamondoid containing materials discussed in previous sections of this description. An exemplary field emission cathode comprising a diamondoid is shown in FIG. 10.

Figure 10:
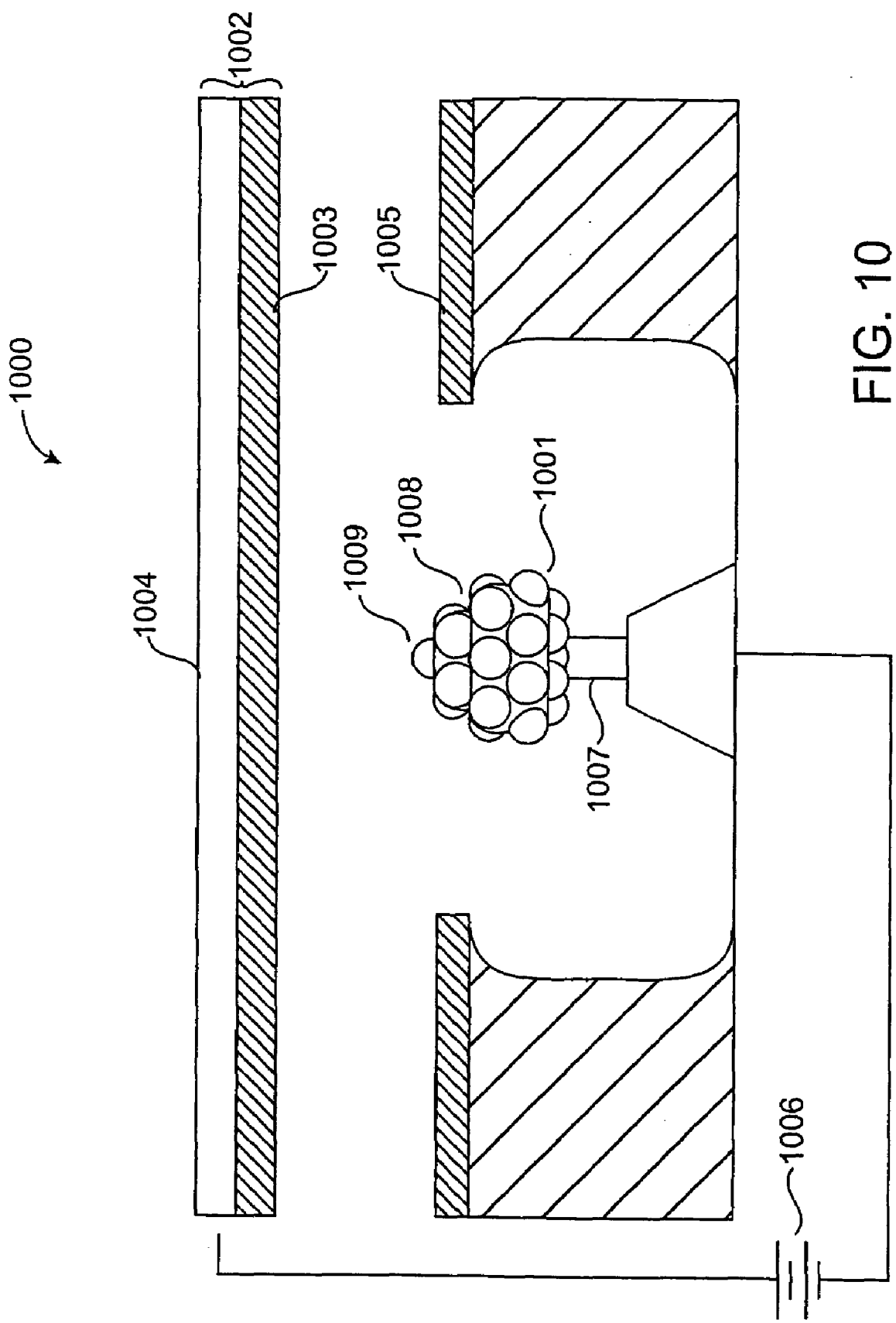
FIG. 10 illustrates schematically a cross-section of a field emission cathode, illustrating where a diamondoid or diamondoid-containing material may be used as a cold cathode filament, taking advantage of the negative electron affinity of a diamondoid surface.

Referring to FIG. 10, a field emission device shown generally at 1000 comprises a diamondoid filament 1001, which acts as a cathode for the device 1000, and a faceplate 1002 on which a phosphorescent coating 1003 has been deposited. The anode for the device may be either a conductive layer 1004 positioned behind the phosphorescent coating 1003, or an electrode 1005 positioned adjacent to the filament 1001. During operation, a voltage from a power supply 1006 is applied between the filament electrode 1007, and the anode of the device, either electrode 1004 or 1005. A typical operating voltage (that is, the potential difference between the cathode and the anode) is less than about 10 volts. This is what allows the cathode to be operated in a so-called "cold" configuration. A typical electronic affinity for a diamondoid surface is contemplated to be less than about 3 eV, and in other embodiments it may be negative. An electron affinity that is less than about 3 eV is considered to be a "low positive value."

Although a diamond material is generally thought to be electrically insulating, the diamondoid filament 1001 may be small enough to allow electrons to tunnel (in a quantum mechanical sense) from the filament electrode 1007 to an opposite surface of the diamondoid, which may be the surface 1008 or the tip 1009. It will be appreciated by the skilled in the art that it is not essential for the diamondoid filament 1001 to have an apex or tip 1009, since the surface of the diamondoid is hydrogenated and $sp^3$-hybridized. In an alternative embodiment, the surface of the cathode may comprise a diamondoid-containing material that is at least partially derivatized such that the surface comprises both $sp^2$ and $sp^3$-hybridization.

An advantage of this embodiment of the present invention is that much greater resolution of the device may be realized relative to a conventional field emission device because of the small size of a typical diamondoid, derivatized diamondoid, self-assembled diamondoid structure, or diamondoid aggregate.

Many modifications of the exemplary embodiments of the invention disclosed above will readily occur to those skilled in the art. Accordingly, the invention is to be construed as including all structure and methods that fall within the scope of the appended claims.

What is claimed is:

1. A thermally conductive material for removing the heat dissipated by an integrated circuit, the thermally conductive material comprising a diamondoid-containing material, wherein the diamondoid-containing material is a diamondoid-containing polymer, a diamondoid-containing sintered ceramic, a diamondoid ceramic composite, a CVD diamondoid film, a diamondoid-containing fiber, or a self-assembled diamondoid film.

2. The thermally conductive material of claim 1, wherein the diamondoid comprises a derivatized diamondoid.

3. The thermally conductive material of claim 1, wherein the diamondoid comprises an underivatized diamondoid.

4. The thermally conductive material of claim 1, wherein the diamondoid is a lower diamondoid.

5. The thermally conductive material of claim 1, wherein the diamondoid is a higher diamondoid.

6. The thermally conductive material of claim 5, wherein the diamondoid is selected from the group consisting of tetramantane, pentamantane, hexamantane, heptamantane, octamantane, nonamantane, decamantane, and undecamantane.

7. The thermally conductive material of claim 1, wherein the material is a film.

8. The thermally conductive material of claim 1, wherein the material is a fiber.

9. The thermally conductive material of claim 1, wherein the diamondoid content of the thermally conductive material ranges from about 1 to 100 percent by weight for the diamondoid-containing polymer, about 1 to 99.9 percent by weight for the diamondoid-containing sintered ceramic, about 1 to 100 percent by weight for the CVD diamondoid film, and about 1 to 99.99 percent by weight for the self-assembled diamondoid film.

10. The thermally conductive material of claim 1, wherein the thermal conductivity of the material is at least 200 W/m K.

11. The thermally conductive material of claim 1, wherein the thermal conductivity of the material is at least 500 W/m K.

12. The thermally conductive material of claim 1, wherein the thermal conductivity of the material is at least 1,000 W/m K.

* * * * *